(12) United States Patent
Ito et al.

(10) Patent No.: US 9,176,042 B2
(45) Date of Patent: Nov. 3, 2015

(54) MICROCHIP AND PARTICULATE ANALYZING DEVICE

(75) Inventors: Tatsumi Ito, Kanagawa (JP); Shoji Akiyama, Kanagawa (JP); Masaya Kakuta, Tokyo (JP); Takeshi Yamasaki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 352 days.

(21) Appl. No.: 13/580,912

(22) PCT Filed: Feb. 18, 2011

(86) PCT No.: PCT/JP2011/000902
§ 371 (c)(1),
(2), (4) Date: Aug. 23, 2012

(87) PCT Pub. No.: WO2011/108206
PCT Pub. Date: Sep. 9, 2011

(65) Prior Publication Data
US 2013/0008240 A1    Jan. 10, 2013

(30) Foreign Application Priority Data

Mar. 1, 2010 (JP) ................................ 2010-043968

(51) Int. Cl.
*G01N 1/00* (2006.01)
*G01N 15/14* (2006.01)
(Continued)

(52) U.S. Cl.
CPC ...... *G01N 15/1404* (2013.01); *B01L 3/502776* (2013.01); *G01N 15/1056* (2013.01); *G01N 2015/1413* (2013.01)

(58) Field of Classification Search
CPC ........... G01N 1/405; G01N 1/10; G01N 1/38; B01L 2400/0406

USPC ......................................................... 73/61.59
See application file for complete search history.

(56) References Cited

U.S. PATENT DOCUMENTS 8,246,805 B2    8/2012  Shinoda
2005/0161326 A1 7/2005  Morita et al.
(Continued)

FOREIGN PATENT DOCUMENTS

CN    101609088    12/2009
JP    63-228040     9/1988
(Continued)

OTHER PUBLICATIONS

Intellectual Property Office of Singapore, Invitation to Respond to Written Opinion issued in connection with Singapore Patent Application No. 201205906-9, dated Nov. 4, 2014. (14 pages).
(Continued)

*Primary Examiner* — Hezron E Williams
*Assistant Examiner* — Rodney T Frank
(74) *Attorney, Agent, or Firm* — K&L Gates LLP

(57) ABSTRACT

A microchip is provided which includes a first introduction channel, second introduction channels arranged to sandwich the first introduction channel and merged with the first introduction channel from both sides, and a merge channel connected to the first introduction channel and the second introduction channels, where fluids fed from the first and the second introduction channels are merged and flow, wherein the merge channel has a tapered portion formed so that a channel width in a sandwiching direction along which the first introduction channel is sandwiched by the second introduction channels gradually increases along a fluid feeding direction.

26 Claims, 21 Drawing Sheets

(51) Int. Cl.
   *B01L 3/00*   (2006.01)
   *G01N 15/10*   (2006.01)

(56) References Cited

U.S. PATENT DOCUMENTS

| | | | |
|---|---|---|---|
| 2005/0266582 A1* | 12/2005 | Modlin et al. | 436/164 |
| 2008/0218753 A1 | 9/2008 | Chang et al. | |
| 2009/0201504 A1 | 8/2009 | Ho et al. | |
| 2010/0027372 A1 | 2/2010 | Ozawa et al. | |

FOREIGN PATENT DOCUMENTS

| | | |
|---|---|---|
| JP | 05-034262 | 2/1993 |
| JP | 06-281557 | 10/1994 |
| JP | 07-119686 | 12/1995 |
| JP | 09-508704 | 9/1997 |
| JP | 2000-506266 | 5/2000 |
| JP | 2003-107099 | 4/2003 |
| JP | 2005-077397 | 3/2005 |
| JP | 2005-513476 | 5/2005 |
| JP | 2005-144356 | 6/2005 |
| JP | 2005-195540 | 7/2005 |
| JP | 2005-214691 | 8/2005 |
| JP | 2006-073188 | 3/2006 |
| JP | 2007-514522 | 6/2007 |
| JP | 2007-225438 | 9/2007 |
| JP | 2009-276119 | 11/2009 |
| JP | 2010-025911 | 2/2010 |
| JP | 2010-029790 | 2/2010 |

OTHER PUBLICATIONS

Office Action issued in connection with Japanese Patent Application No. 2014-207146, dated Jun. 30, 2015. (4 pages).

* cited by examiner

US 9,176,042 B2

MICROCHIP AND PARTICULATE ANALYZING DEVICE

CROSS REFERENCES TO RELATED APPLICATIONS

The present application is a national stage of International Application No. PCT/JP2011/000902 filed on Feb. 18, 2011 and claims priority to Japanese Patent Application No. 2010-043968 filed on Mar. 1, 2010, the disclosure of which is incorporated herein by reference.

BACKGROUND

The present invention relates to a microchip and a particulate analyzing device. More particularly, the present invention relates to a microchip or the like for optically, electrically or magnetically analyzing the characteristics of particulates such as cells or microbeads in channels.

In recent years, microchips have been developed in which an area and/or a channel or channels for performing chemical and biological analyses are provided by application of micro-machining techniques used in the semiconductor industry. These microchips have begun to be utilized for electrochemical detectors in liquid chromatography, small electrochemical sensors in medical service sites, and the like.

Analytical systems using such microchips are called micro-TAS (micro-Total-Analysis System), lab-on-a-chip, bio chip or the like, and is paid attention to as a technology by which chemical and biological analyses can be enhanced in speed, efficiency and level of integration or by which analyzing devices can be reduced in size.

The micro-TAS, which enables analysis with a small amount of sample and enables disposable use of microchips, is expected to be applied particularly to biological analyses where precious trace amounts of samples or a multiplicity of specimens are treated.

An application example of the micro-TAS is a particulate analyzing technology in which characteristics of particulates such as cells and microbeads are analyzed optically, electrically or magnetically in channels arranged on microchips. In the particulate analyzing technology, fractional collection of a population satisfying a predetermined condition or conditions from among particulates on the basis of analytical results of the particulates is also conducted.

Patent Literature 1, for example, discloses "a particulate fractionation microchip having a channel for introducing particulate-containing solution, and a sheath flow forming channel arranged on at least one lateral side of the introducing channel." The particulate fractionation microchip further has "a particulate measuring section for measuring the particulates introduced, at least two particulate fractionating channels disposed on the downstream side of the particulate measuring section so as to perform fractional collection of the particulates, and at least two electrodes disposed in the vicinity of channel ports opening from the particulate measuring section into the particulate fractionating channels so as to control the moving direction of the particulates."

The particulate fractionation microchip disclosed in Patent Literature 1, typically, is so designed that fluid laminar flows are formed by a "trifurcated channel" having a channel for introducing a particulate-containing solution and two sheath flow forming channels (see "FIG. 1" of the literature).

FIGS. 17A and 17B show a trifurcated channel structure according to related art (FIG. 17A), and sample liquid laminar flows formed by the channel structure (FIG. 17B). In the trifurcated channel, a sample liquid laminar flow passing through a channel 101 in the direction of solid-line arrow in FIG. 17A can be sandwiched, from the left and right sides, by sheath liquid laminar flows introduced through channels 102, 102 in the directions of dotted-line arrows in the figure. By this, as shown in FIG. 17B, the sample liquid laminar flow can be fed through the center of the channel. Incidentally, in FIG. 17B, the sample liquid laminar flow is depicted in solid lines, and the channel structure in dotted lines.

According to the trifurcated channel shown in FIGS. 17A and 17B, the sample liquid laminar flow is sandwiched by the sheath liquid laminar flows from the left and right sides, whereby with respect to the sandwiching direction (the Y-axis direction in FIGS. 17A and 17B), the sample liquid laminar flow can be fed in the state of being deflected to an arbitrary position in the channel. With respect to the vertical direction (the Z-axis direction in FIGS. 17A and 17B) of the channel, however, it has been very difficult to control the sample liquid feeding position. In other words, in the trifurcated channel according to related art, it has only been possible to form the sample laminar flow that is oblong in the Z-axis direction.

Therefore, the microchip having the trifurcated channel according to related art has the problem that in the case where, for example, a particulate-containing solution as a sample liquid is made to flow through a channel and subjected to optical analysis, there would be a dispersion of the feeding position of the particulates in the vertical direction (depth direction) of the channel. Therefore, there has been the problem that the flowing speed of particulates differs depending on the feeding position of the particulates, variation of detection signals increases, and the accuracy of analysis is degraded.

Patent Literature 2 discloses a channel structure that introduces a sample liquid into the center of a sheath liquid laminar flow from an opening at the center of the channel through which the sheath liquid laminar flow is fed to thereby feed the sample liquid laminar flow being surrounded by the sheath liquid laminar flow (see FIGS. 2 and 3 of the literature). The channel structure enables the sample liquid to be introduced into the center of the sheath liquid laminar flow, thereby eliminating the dispersion of the feeding position of the particulates in the depth direction of the channel, so that the high accuracy of analysis can be obtained.

FIGS. 18A and 18B show a channel structure according to related art applied for introducing a sample liquid to the center of a sheath liquid laminar flow (FIG. 18A), and a sample liquid laminar flow formed by the channel structure (FIG. 18B). In this channel structure, the sheath liquid laminar flow is introduced into each of channels 102 and 102 in the direction of arrow T in FIG. 18A and fed to a channel 103. Then, the sample liquid fed to a channel 101 in the direction of arrow S can be introduced from an opening 104 to the center of the sheath liquid laminar flow fed through the channel 103. The sample liquid laminar flow can be thereby fed, being converged to the center of the channel 103, as shown in FIG. 18B. In FIG. 18B, the sample liquid laminar flow is depicted in solid lines, and the channel structure in dotted lines.

On the other hand, in Patent Literature 2, it is pointed out that, when introducing the sample liquid laminar flow into the sheath liquid laminar flow in such a channel structure, turbulence occurs in the sample liquid laminar flow, which raises the case where the sample liquid laminar flow is not a flat and stable laminar flow (see the rows 12 to 46 in the right column on page 4 of the literature). Note that "flat laminar flow" indicates a laminar flow converted in the depth direction (the Z-axis direction) of the channel in FIGS. 18A and 18B, and "non-flat laminar flow" indicates a laminar flow dispersed and spread in the depth direction of the channel.

In the above Patent Literature, it is proposed to provide the opening of the channel through which the sample liquid laminar flow is introduced with a pair of plate projections (see the reference numeral 18 in FIG. 10 of the literature) or the like in order to suppress the turbulence (wake) of the laminar flow at the merging portion of the sample liquid laminar flow and the sheath liquid laminar flows. The plate projections 18 extend from the opening wall of the channel through which the sample liquid laminar flow is introduced in the flowing direction of the sample liquid laminar flow and guides the sample liquid flowing out from the opening.

CITATION LIST

Patent Literature

PTL 1: Japanese Patent Laid-open No. 2003-107099
PTL 2: Japanese Examined Patent Publication No. 7-119686

SUMMARY

Technical Problem

With the plate projections 18 disclosed in the above Patent Literature 2, it is possible to guide the sample liquid flowing out from the opening and let the sample liquid flow through the channel as a stable laminar flow converged in the depth direction of the channel.

However, the channel structure is complicated when such a guide structure is provided at the opening of the channel through which the sample liquid laminar flow is introduced. Further, it is necessary to laminate three or more substrate onto one another in order to form such a channel structure on a microchip. Therefore, high accuracy is needed for the formation of the channel structure on each substrate and the lamination of the substrates, which increases the manufacturing cost of the microchip.

In light of the foregoing, it is desirable to provide a microchip capable of feeding a sample liquid laminar flow converged to the center of a channel and easily manufacturable.

Solution to Problem

According to an embodiment of the present invention, there is provided a microchip which includes a first introduction channel, second introduction channels arranged to sandwich the first introduction channel and merged with the first introduction channel from both sides, and a merge channel connected to the first introduction channel and the second introduction channels, where fluids fed from the first and the second introduction channels are merged and flow, wherein the merge channel has a tapered portion formed so that a channel width in a sandwiching direction along which the first introduction channel is sandwiched by the second introduction channels gradually increases along a fluid feeding direction. In the microchip, the merge channel may have a tapered portion formed so that a channel depth in a direction perpendicular to a plane containing the first introduction channel and the second introduction channels gradually decreases along a fluid feeding direction.

According to another embodiment of the present invention, there is provided a microchip which includes a first introduction channel, two second introduction channels arranged to sandwich the first introduction channel and merged with the first introduction channel from both sides, and a merge channel connected to the first introduction channel and the second introduction channels, where fluids fed from the first and the second introduction channels are merged and flow, wherein the merge channel has a tapered portion formed so that a channel depth in a direction perpendicular to a plane containing the first introduction channel and the second introduction channels gradually decreases along a fluid feeding direction.

In the above microchip, a channel depth of the first introduction channel may be smaller than a channel depth of the second introduction channels, and a communicating port of the first introduction channel to the merge channel may be disposed at a substantially center position in a channel depth direction of the second introduction channels.

Further, a communicating port of the first introduction channel to the merge channel preferably opens in an area including respective channel walls of the second introduction channels.

In the above microchip, a contracted portion formed so that the channel width gradually decreases again along the fluid feeding direction may be disposed on a downstream side in the feeding direction of the tapered portion formed so that the channel width gradually increases along the fluid feeding direction.

According to yet another embodiment of the present invention, there is provided a particulate analyzing device which includes the above microchip, wherein the microchip has a detecting portion that detects a particulate contained in a fluid fed from the first introduction channel on a downstream side of the contracted portion in the merge channel.

It should be noted that the "particulates" in the present embodiment widely include microscopic bioparticles such as cells, microorganisms, liposome, etc. as well as synthetic particles such as latex particles, gel particles, industrial particles, etc.

The microscopic bioparticles include chromosome, liposome, mitocondria, organelle, etc. which constitute various cells. The cells here include animal cells (blood corpuscle cells, etc.) and plant cells. The microorganisms includes bacteria such as colibacillus, etc., viruses such as tobacco mosaic virus, etc., and fungi such as yeast, etc. Further, the microscopic bioparticles may include also microscopic biopolymers such as nucleic acid, proteins, and complexes thereof.

The industrial particles may be, for example, organic or inorganic polymer materials, metals or the like. The organic polymer materials include polystyrene, stylenevinylbenzene, and polymethyl methacrylate. The inorganic polymer materials include glass, silica, and magnetic materials. The metals include gold colloid and aluminum. The shape of these particulates is usually spherical, but may be non-spherical. Besides, the particulates are not particularly limited as to size, mass or the like.

Advantageous Effects of Invention

According to the embodiments of the present invention described above, a microchip capable of feeding a sample liquid laminar flow converged to the center of a channel and easily manufacturable is provided.

BRIEF DESCRIPTION OF THE FIGURES

FIGS. 1A and 1B are schematic diagrams illustrating a channel structure on a microchip according to a first embodiment of the present invention, in which FIG. 1A shows a top view and FIG. 1B shows a sectional view;

FIGS. 2A, 2B and 2C are schematic diagrams illustrating sections of a merge channel 12 of the microchip according to the first embodiment of the present invention, in which FIG. 2A shows section P-P, FIG. 2B shows section Q-Q, and FIG. 2C shows section R-R, respectively in FIGS. 1A and 1B;

FIG. 3 is a schematic diagram illustrating a structure of a communicating port 111 of the microchip according to the first embodiment of the present invention;

FIGS. 4A and 4B are schematic diagrams illustrating a structure of the communicating port 111 of the microchip according to the first embodiment of the present invention (FIG. 4A) and an opening 104 of a channel structure according to related art shown in FIGS. 18A and 18B (FIG. 4B);

FIGS. 5A, 5B and 5C are schematic diagrams illustrating alternative examples of a tapered portion 122 of the microchip according to the first embodiment of the present invention, in which the upper part shows a top view and the lower part shows a sectional view;

FIGS. 6A and 6B are schematic diagrams illustrating a channel structure on a microchip according to a second embodiment of the present invention, in which FIG. 6A shows a top view and FIG. 6B shows a sectional view;

FIGS. 7A, 7B and 7C are schematic diagrams illustrating sections of a merge channel 12 of the microchip according to the second embodiment of the present invention, in which FIG. 7A shows section P-P, FIG. 7B shows section Q-Q, and FIG. 7C shows section R-R, respectively in FIGS. 6A and 6B;

FIG. 8 is a schematic diagram illustrating an alternative example of a tapered portion 123 of the microchip according to the second embodiment of the present invention, in which the upper part shows a top view and the lower part shows a sectional view;

FIG. 9 is a schematic diagram illustrating a taper angle in a depth direction of a channel of the tapered portion 123 of the microchip according to the second embodiment of the present invention, in which the upper part shows a top view and the lower part shows a sectional view;

FIGS. 10A and 10B are schematic diagrams illustrating an alternative example of a tapered portion 123 and a contracted position 121 of the microchip according to the second embodiment of the present invention, in which FIG. 10A shows a top view and FIG. 10B shows a sectional view;

FIGS. 11A and 11B are schematic diagrams illustrating a channel structure on a microchip according to a third embodiment of the present invention, in which FIG. 11A shows a top view and FIG. 11B shows a sectional view;

FIGS. 12A, 12B and 12C are schematic diagrams illustrating sections of a merge channel 12 of the microchip according to the third embodiment of the present invention, in which FIG. 12A shows section P-P, FIG. 12B shows section Q-Q, and FIG. 12C shows section R-R, respectively in FIGS. 11A and 11B;

FIG. 13 is a schematic diagram illustrating an alternative example of tapered portions 122 and 123 of the microchip according to the third embodiment of the present invention, in which the upper part shows a top view and the lower part shows a sectional view;

FIGS. 14A and 14B are schematic diagrams illustrating an alternative example of a tapered portion 123 and a contracted position 121 of the microchip according to the third embodiment of the present invention, in which FIG. 14A shows a top view and FIG. 14B shows a sectional view;

FIGS. 15A and 15B are diagrams illustrating a manufacturing method of a microchip according to an embodiment of the present invention, which show top schematic diagrams of substrates constituting a chip;

FIGS. 16A and 16B are schematic diagrams illustrating a manufacturing method of a microchip according to an embodiment of the present invention, in which FIG. 16B shows a section along P-P in FIG. 16A;

FIGS. 17A and 17B are schematic diagrams illustrating a trifurcated channel structure according to related art (FIG. 17A), and sample liquid laminar flows formed by the channel structure (FIG. 17B);

FIGS. 18A and 18B are schematic diagrams illustrating a channel structure according to related art applied for introducing a sample liquid to the center of sheath liquid laminar flows (FIG. 18A), and sample liquid laminar flows formed by the channel structure (FIG. 18B).

FIGS. 19A and 19B are schematic diagrams illustrating the channel structure according to related art shown in FIGS. 18A and 18B, in which FIG. 19A shows a top view and FIG. 19B shows a sectional view;

FIGS. 20A, 20B and 20C are schematic diagrams illustrating a fluid velocity vector field in the channel structure according to related art shown in FIGS. 18A and 18B, in which FIG. 20A shows section P-P, FIG. 20B shows section Q-Q, and FIG. 20C shows section R-R, respectively in FIGS. 19A and 19B; and

FIG. 21 is a schematic diagram illustrating a fluid velocity vector field in the channel structure according to related art shown in FIGS. 18A and 18B.

Additional features and advantages are described herein, and will be apparent from the following Detailed Description and the figures.

DETAILED DESCRIPTION

Preferred embodiments for carrying out the present invention will be described hereinafter with reference to the drawings. Note that the embodiments described below are typical exemplary embodiments of the present invention, and the invention is not to be narrowly construed due to the embodiments. The description will be given in the following order.

1. Fluid Velocity Vector Field in Channel Structure According to Related Art
2. Microchip According to First Embodiment of Invention
3. Alternative Example of Channel Structure of Microchip According to First Embodiment
4. Microchip According to Second Embodiment of Invention
5. Alternative Example of Channel Structure of Microchip According to Second Embodiment
6. Microchip According to Third Embodiment of Invention
7. Alternative Example of Channel Structure of Microchip According to Third Embodiment
8. Manufacturing of Microchip According to Invention
9. Particulate Analyzing Device According to Invention 1. Fluid Velocity Vector Field in Channel Structure According to Related Art The channel structure according to related art which is applied for introducing a sample liquid to the center of a sheath liquid laminar flow, shown in FIGS. 18A and 18B, has the problem that, when introducing the sample liquid laminar flow into the sheath liquid laminar flow, turbulence occurs in the sample liquid laminar flow, and the sample liquid laminar flow is not converted to the center of the channel.

Figure 19:
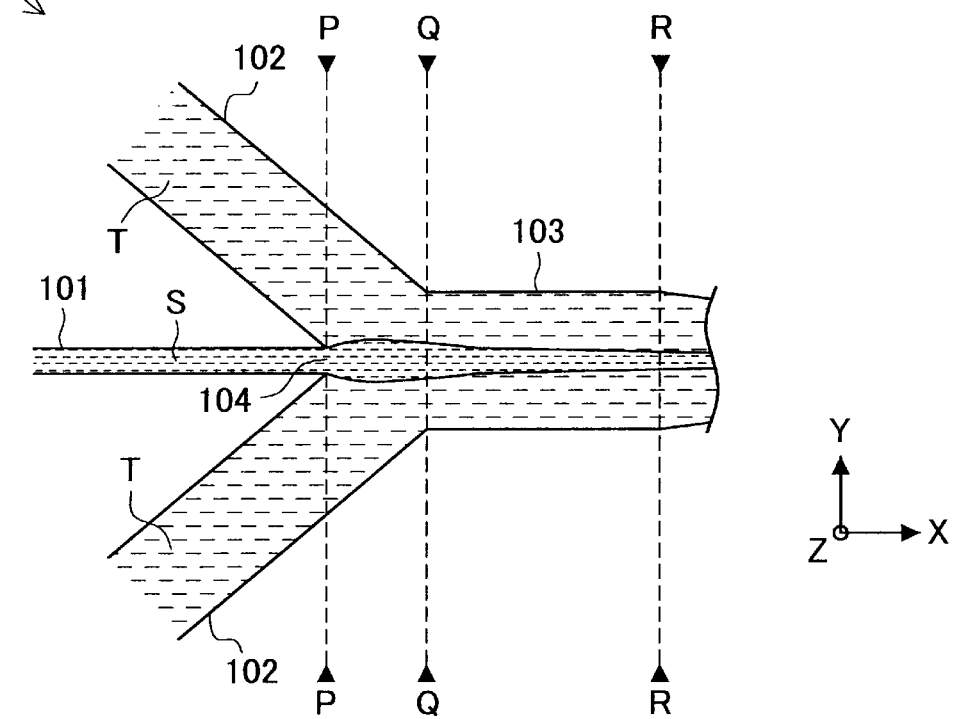
[FIG. 19]
Figure 19:
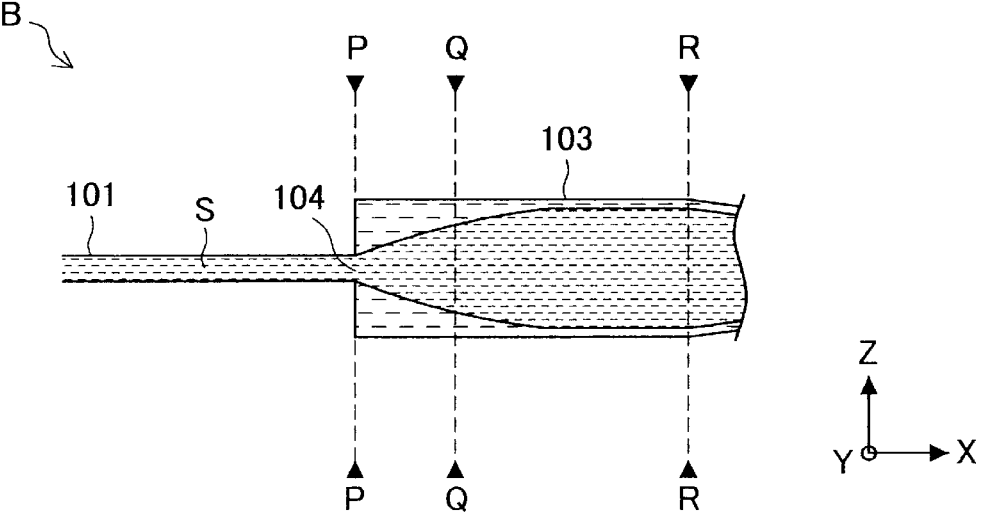

Specifically, referring to FIGS. 19A and 19B, in the case where a sample liquid laminar flow S is introduced from an opening 104 to the center of sheath liquid laminar flows T respectively introduced to channels 102 and 102 and flowing through a channel 103, the sample liquid laminar flow S is dispersed in the depth direction of the channel (the Z-axis direction) in some cases. If the sample liquid laminar flow S is not converted to the center of the channel, the feeding position of the particulates contained in the sample liquid laminar flow S is dispersed in the depth direction of the channel, and therefore, the detection signal of the particulates also varies, which causes degradation of the accuracy of analysis.

The inventors of the present invention have conducted numerical calculation of the fluid velocity vector field (flow field) in the channel structure in order to find a factor of the turbulence of the sample liquid laminar flow occurring in the channel structure according to related art. As a result, they have found that the spiral flow field generated after the merging of the sample liquid laminar flow and the sheath liquid laminar flows causes the turbulence of the sample liquid laminar flow.

The fluid velocity vector field in the channel structure according to related art is described with reference to FIGS. 19A and 19B and FIGS. 20A to 20C. FIGS. 20A to 20C are schematic sectional diagrams of the channel structure according to related art, in which FIG. 20A shows section P-P, FIG. 20B shows section Q-Q, and FIG. 20C shows section R-R, respectively in FIGS. 19A and 19B.

When the sample liquid laminar flow S is introduced from the opening 104 into the center of the sheath liquid laminar flow T fed through the channel 103, a high velocity vector appears at the center in the depth direction of the channel immediately after the introduction (see the arrows in FIG. 20A). It is considered that the high velocity vector occurs because the merged sample liquid laminar flow S and sheath liquid laminar flows T are concentrated on the center of the depth direction of the channel for flowing faster.

Further, in the process that the flow fields from the channel 101 and the channels 102 and 102 are merged into one flow field, a high velocity vector occurring at the center in the depth direction of the channel grows into the flow field that rotates in the Z-axis positive or negative direction as shown in FIG. 20B, and further grows into the spiral flow field as shown in FIG. 20C. Then, it has been founded that the sample liquid laminar flow S is stretched out in the Z-axis positive and negative direction and dispersed in the depth direction of the channel. It has been also found that the deformation of the sample liquid laminar flow S due to the spiral flow field becomes more significant depending on the flow rate of the sheath liquids fed from the channels 102 and 102.

Furthermore, the inventors of the present invention have found, as a result of the numerical calculation of the fluid velocity vector field (flow field), that a slow flow field occurring near the opening for introducing the sample liquid laminar flow into the center of the sheath liquid laminar flow causes the turbulence of the sample liquid laminar flow.

Figure 18:
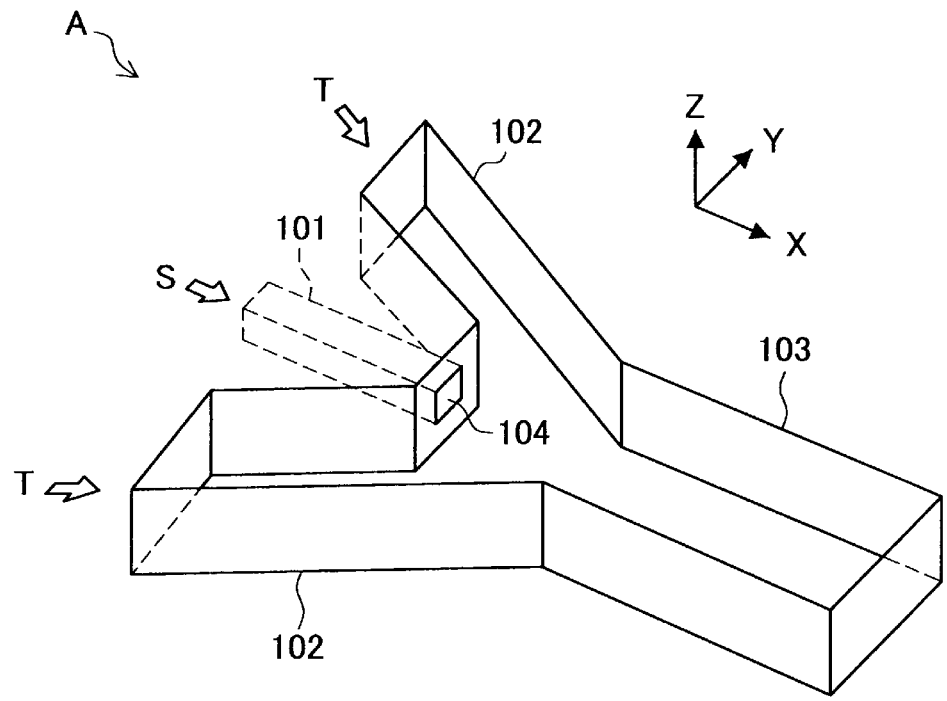
[FIG. 18]
Figure 18:
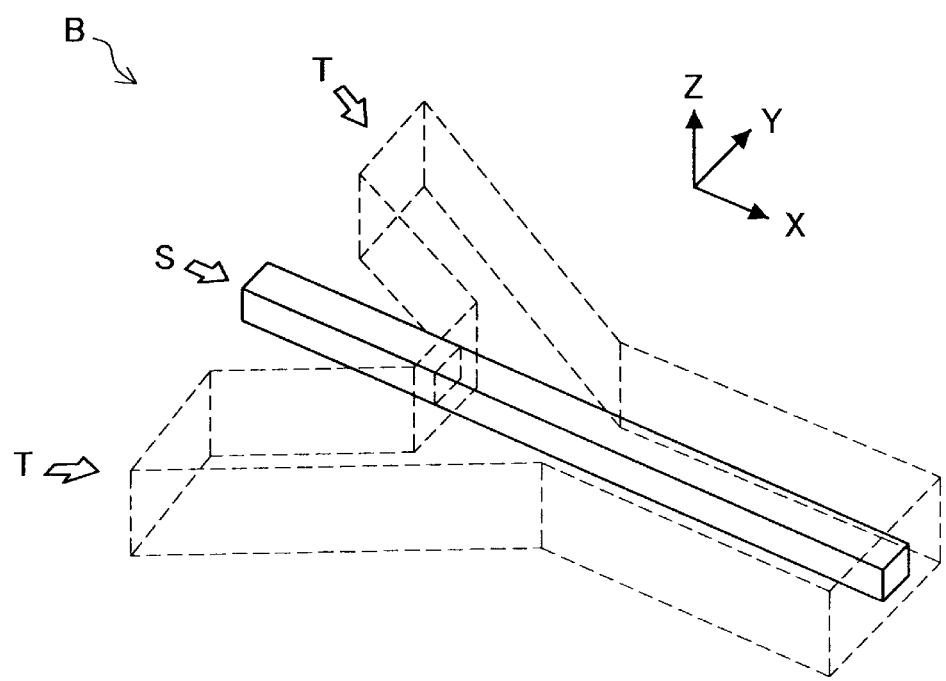
Figure 21:
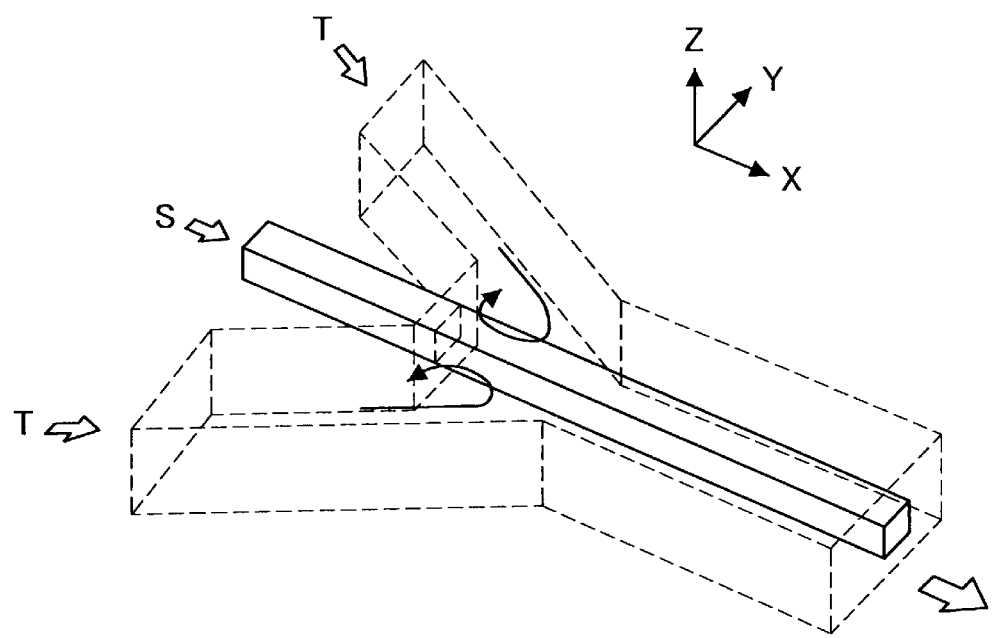
[FIG. 21]

FIG. 21 schematically illustrates a slow flow field occurring in the vicinity of an opening 104 of the channel structure according to related art, shown in FIGS. 18A and 18B, which is applied for introducing the sample liquid to the center of the sheath liquid laminar flow.

In the vicinity of the opening 104, a shear force occurs between the sheath liquid laminar flows T and the sample liquid laminar flow S due to the merging of the sheath liquids fed from the channels 102 and 102 and the sample liquid flowing out from the opening 104. It has been found that, by the shear force, a slow velocity vector occurs in the vicinity of the opening 104, and an unstable flow field with a stagnant flow is generated. Due to the stagnant flow field, the sample liquid laminar flow S becomes unstable and dispersed in the depth direction of the channel. It has been also found that the deformation of the sample liquid laminar flow S due to the stagnant flow field becomes more significant as the flow rate of the sample liquid flowing out of the opening 104 is lower.

2. Microchip According to First Embodiment of Invention

A first feature of a microchip according to an embodiment of the present invention is to provide a channel structure that suppresses the above-described spiral flow field generated after merging of the sample liquid laminar flow and the sheath liquid laminar flows and thereby avoids the turbulence of the sample liquid laminar flow. A second feature of a microchip according to an embodiment of the present invention is to provide a channel structure that suppresses the above-described stagnant flow field generated in the vicinity of an opening for introducing the sample liquid laminar flow to the center of the sheath liquid laminar flow and thereby avoids the turbulence of the sample liquid laminar flow.

Figure 1:
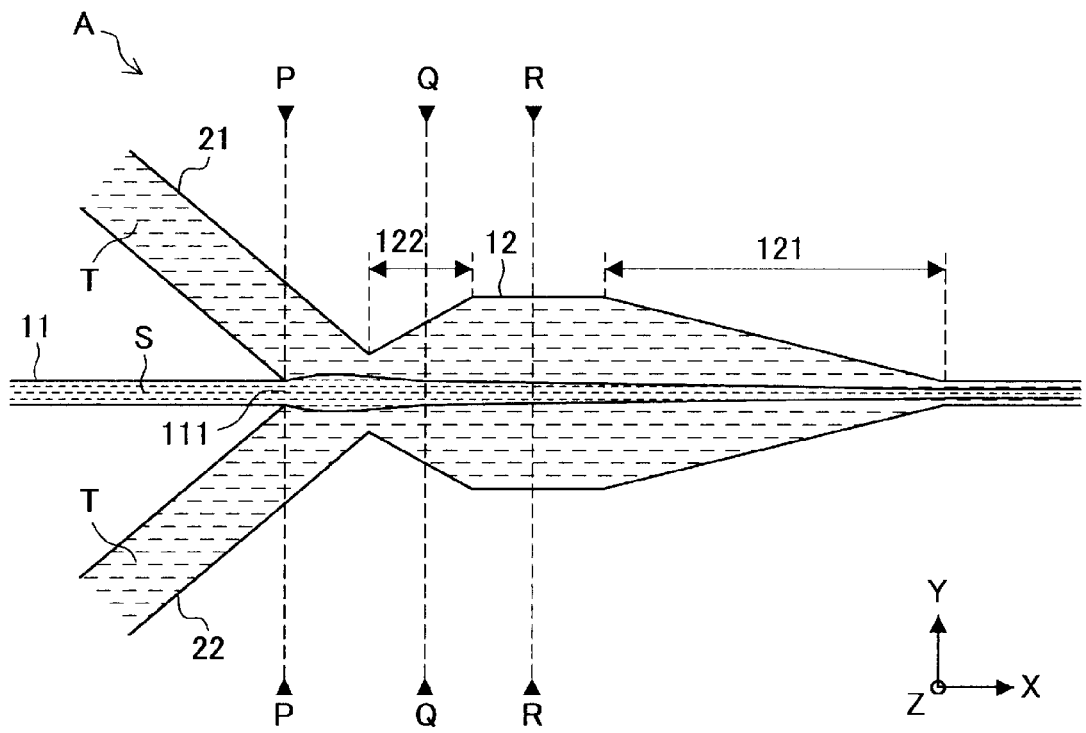
[FIG. 1]
Figure 1:
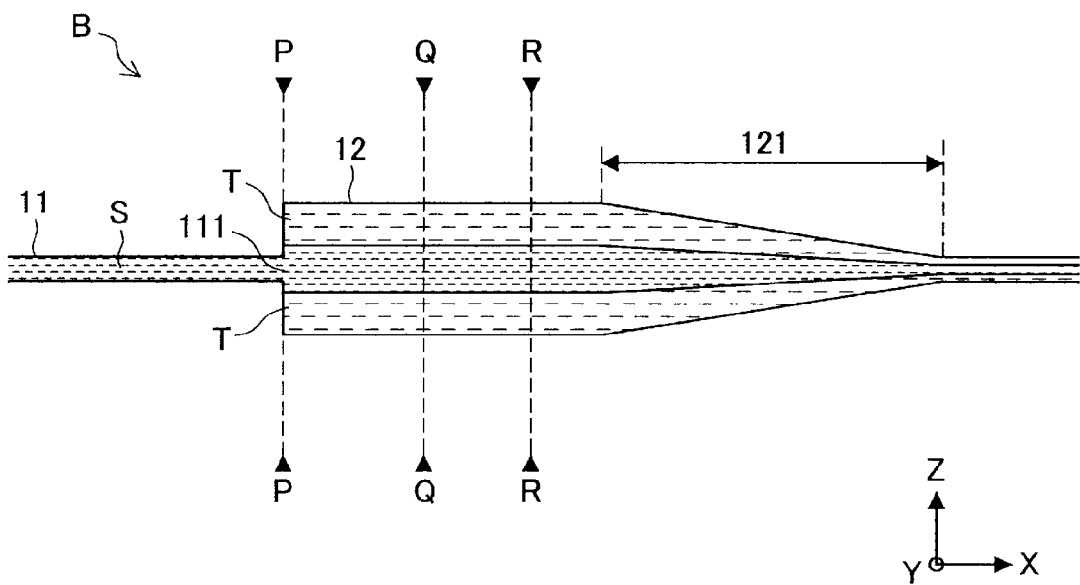

FIGS. 1A and 1B are schematic diagrams illustrating a channel structure formed on a microchip according to a first embodiment of the present invention, in which FIG. 1A shows a top view and FIG. 1B shows a sectional view.

In the figures, the reference numeral 11 indicates a first introduction channel (which is referred to hereinafter as a sample liquid introduction channel 11) through which a first fluid (referred to hereinafter as a sample liquid) is introduced. The reference numerals 21 and 22 indicate second introduction channels (referred to hereinafter as sheath liquid introduction channels 21 and 22) which are arranged to sandwich the sample liquid introduction channel 11 and merged with the sample liquid introduction channel 11 from the both sides thereof, and through which a second fluid (referred to hereinafter as a sheath liquid) is introduced. Further, the reference numeral 12 indicates a merge channel which is connected to the sample liquid introduction channel 11 and the sheath liquid introduction channels 21 and 22 and through which the sample liquid and the sheath liquids fed from the respective channels are merged and flow.

The sample liquid introduction channel 11 has, at the merging portion with the sheath liquid introduction channels 21 and 22, a communicating port 111 for introducing the sample liquid into the center of the merge channel 12 through which the sheath liquid laminar flow T flows. The channel depth of the sample liquid introduction channel 11 in the Z-axis direction is designed to be smaller than the channel depth of the sheath liquid introduction channels 21 and 22, and the communicating port 111 is disposed at substantially the center position in the channel depth direction of the sheath liquid introduction channels 21 and 22. Further, the communicating port 111 is also disposed at substantially the center position in the channel width direction (the Y-axis direction) of the merge channel 12.

By introducing the sample liquid laminar flow S to the center of the sheath liquid laminar flow T from the communicating port 111, the sample liquid laminar flow S can be fed in the state of being surrounded by the sheath liquid laminar flow T (see also FIGS. 2A, 2B and 2C described next). Note that the position where the communicating port 111 is placed is not limited to the center position of the channel depth direction of the sheath liquid introduction channels 21 and 22 and may be in its vicinity, as long as it allows the sample liquid laminar flow S to be fed into the merge channel 12 in the state of being surrounded by the sheath liquid laminar flow T. Likewise, the position of the communicating port 111 in the channel width direction of the merge channel 12 is not limited to the center position and may be in its vicinity.

Figure 20:
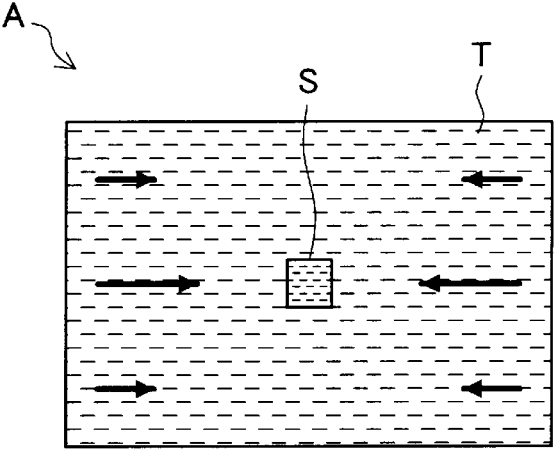
[FIG. 20]
Figure 20:
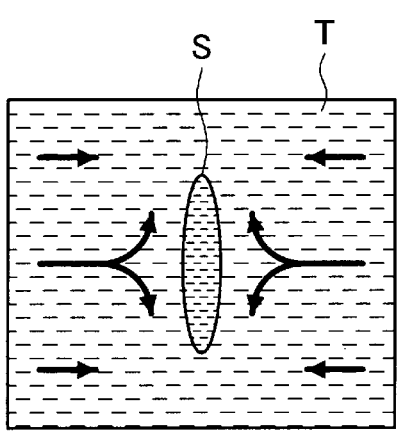
Figure 20:
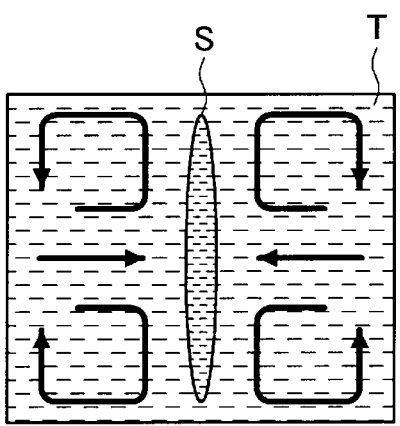

In the figures, the reference numeral 122 indicates a tapered portion that functions to suppress the spiral flow field generated after the merging of the sample liquid laminar flow and the sheath liquid laminar flows illustrated in FIG. 20. The tapered portion 122 is disposed in the merge channel 12 in close proximity to the merging portion of the sample liquid introduction channel 11 with the sheath liquid introduction channels 21 and 22. The tapered portion 122 is formed so that the channel width in the sandwiching direction (the Y-axis direction) along which the sample liquid introduction channel 11 is sandwiched by sheath liquid introduction channels 21 and 22 is enlarged gradually along the feeding direction.

The fluid velocity vector field in the merge channel 12 and the function of the tapered portion 122 are described with reference to FIGS. 1A and 1B and FIGS. 2A to 2C. FIGS. 2A, 2B and 2C are schematic sectional diagrams of the merge channel 12, in which FIG. 2A shows section P-P, FIG. 2B shows section Q-Q, and FIG. 2C shows section R-R, respectively in FIGS. 1A and 1B.

When the sample liquid laminar flow S is introduced from an opening 111 into the center of the sheath liquid laminar flow T flowing through the merge channel 12, a high velocity vector appears at the center in the depth direction of the channel immediately after the introduction (see the dotted-line arrows in FIG. 2A). The high velocity vector occurs because the merged sample liquid laminar flow S and sheath liquid laminar flows T are concentrated on the center of the depth direction of the channel for flowing faster as described earlier.

At the tapered portion 122, when the laminar flow width of the merged sample liquid laminar flow S and sheath liquid laminar flow T is enlarged in the Y-axis direction, a flow field (see the solid-line arrows in FIG. 2B), which is in reverse direction to the high velocity vector generated at the center in the depth direction of the channel, is generated. By generating the reverse flow field, the tapered portion 122 cancels out the flow field generated at the center in the depth direction of the channel and thereby prevents the flow field from growing into the spiral flow field. As a result, the sample liquid laminar flow S is maintained in the state of being converted to the center of the channel without being stretched out in the Z-axis direction by the spiral flow field (see FIGS. 2B and 2C).

In the figures, the reference numeral 121 indicates a contracted portion that functions to narrow down the laminar flow width of the merged sample liquid laminar flow S and sheath liquid laminar flow T in the Y-axis direction and the Z-axis direction. The contracted portion 121 is disposed on the downstream side of the tapered portion 122. The contracted portion 121 is formed so that the channel width is reduced gradually along the feeding direction. Further, the contracted portion 121 is formed so that the channel depth is also reduced gradually along the feeding direction. Specifically, the channel wall of the contracted portion 121 is formed to be narrowed along the feeding direction in the Y-axis and the Z-axis directions, and the contracted portion 121 is formed so that the area of the vertical section with respect to the feeding direction (the X-axis positive direction) decreases gradually. With such a shape, the contracted portion 121 feeds the liquids by narrowing down the laminar flow width of the merged sample liquid laminar flow S and sheath liquid laminar flow T in the Y-axis direction and the Z-axis direction.

Figure 3:
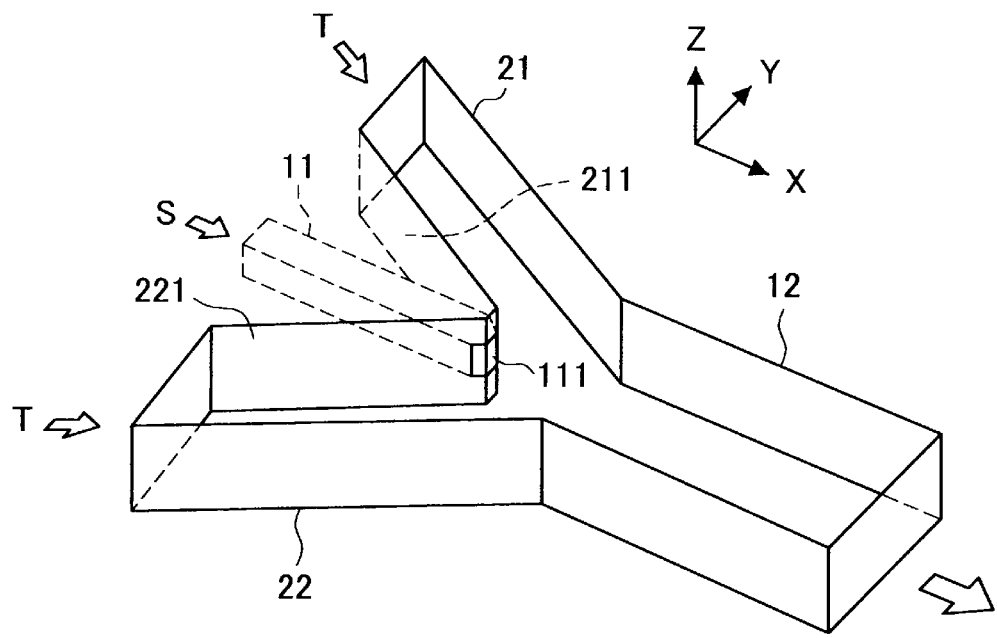
[FIG. 3]
Figure 4:
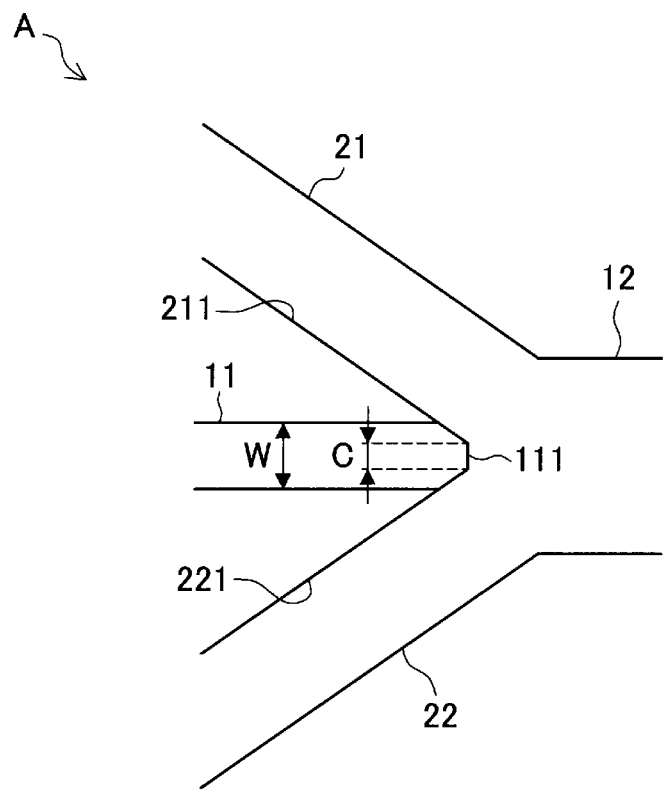
[FIG. 4]
Figure 4:
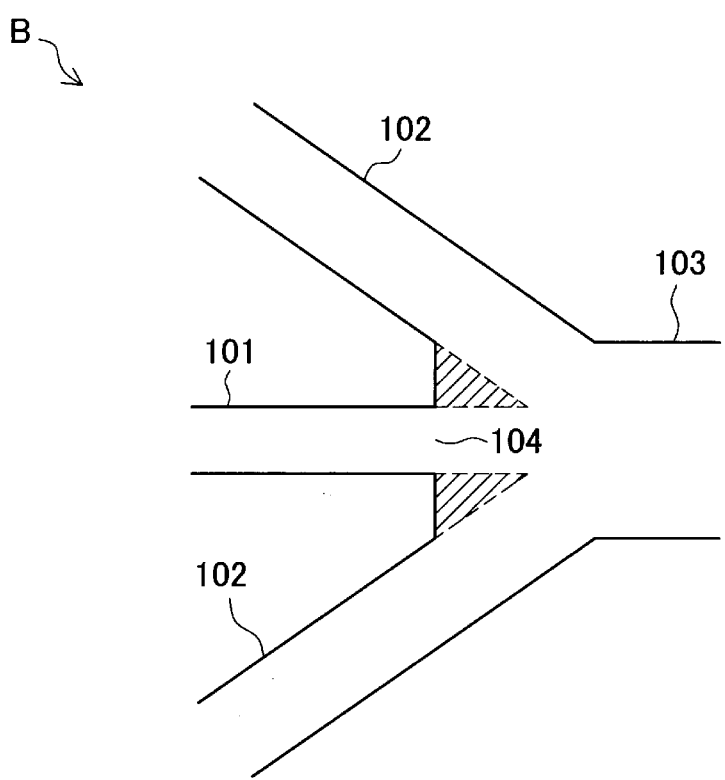

FIG. 3 and FIGS. 4A and 4B are schematic diagrams illustrating a structure of the communicating port 111. The channel depth of the sample liquid introduction channel 11 in the Z-axis direction is designed to be smaller than the channel depth of the sheath liquid introduction channels 21 and 22, and the communicating port 111 is placed at substantially the center position of the channel depth direction of the sheath liquid introduction channels 21 and 22 (see FIG. 3). Further, in order to suppress the stagnant flow field generated in the vicinity, the communicating port 111 opens in an area including channel walls 211 and 221 of the sheath liquid introduction channel 21 and the sheath liquid introduction channel 22.

This is described specifically with reference to FIGS. 4A and 4B. First, a structure of the opening 104 in the channel structure according to related art (see FIGS. 18A and 18B) is described with reference to FIG. 4B. In the channel structure according to related art, by a shear force which occurs between the sheath liquid laminar flows T and the sample liquid laminar flow S due to the merging of the sheath liquids fed from the channels 102 and 102 and the sample liquid flowing out from the opening 104, an unstable flow field with a stagnant flow (the diagonally shaded area in FIG. 4B) is generated in the vicinity of the opening 104 (see also FIG. 21).

In this case, the sample liquid flows out to the stagnant, unstable flow field from the opening 104. Consequently, the sample liquid laminar flow S becomes unstable before coming into contact with the fast-flowing sheath liquids fed from the channels 102 and 102 and dispersed in the depth direction of the channel.

On the other hand, because the communicating port 111 of the microchip according to the embodiment opens in an area including the channel walls 211 and 221 of the sheath liquid introduction channel 21 and the sheath liquid introduction channel 22, the sample liquid flowing out of the communicating port 111 comes into direct contact with the fast-flowing sheath liquids fed through the sheath liquid introduction channels 21 and 22. Consequently, the sample liquid laminar flow S is accelerated by the sheath liquids immediately after flowing out of the communicating port 111 and thereby maintained in the stable state of being converted to the center of the channel without being dispersed in the depth direction.

Note that the shape of the communicating port 111 described herein may be regarded as a shape that the side end of the communicating port 111 of the sample liquid introduction channel 11 is cut out by the channel walls 211 and 221 of the sheath liquid introduction channel 21 and the sheath liquid introduction channel 22. Because the shape of the communicating port 111 is made by the cutout by the channel walls 211 and 221 of the sheath liquid introduction channel 21 and the sheath liquid introduction channel 22, the channel width indicated by the symbol W in FIG. 4A is designed to be smaller than the channel width after cutout indicated by the symbol C.

3. Alternative Example of Channel Structure of Microchip According to First Embodiment FIG. 1A illustrates the case where the tapered portion 122 is disposed in the merge channel 12 on the downstream side of the communicating port 111, which is the merging portion of the sample liquid introduction channel 11 with the sheath liquid introduction channels 21 and 22. However, the position where the tapered portion 122 is disposed is not limited to the position shown in FIG. 1A, as long as it is in close proximity to the merging portion of the sample liquid introduction channel 11 with the sheath liquid introduction channels 21 and 22.

Figure 5:
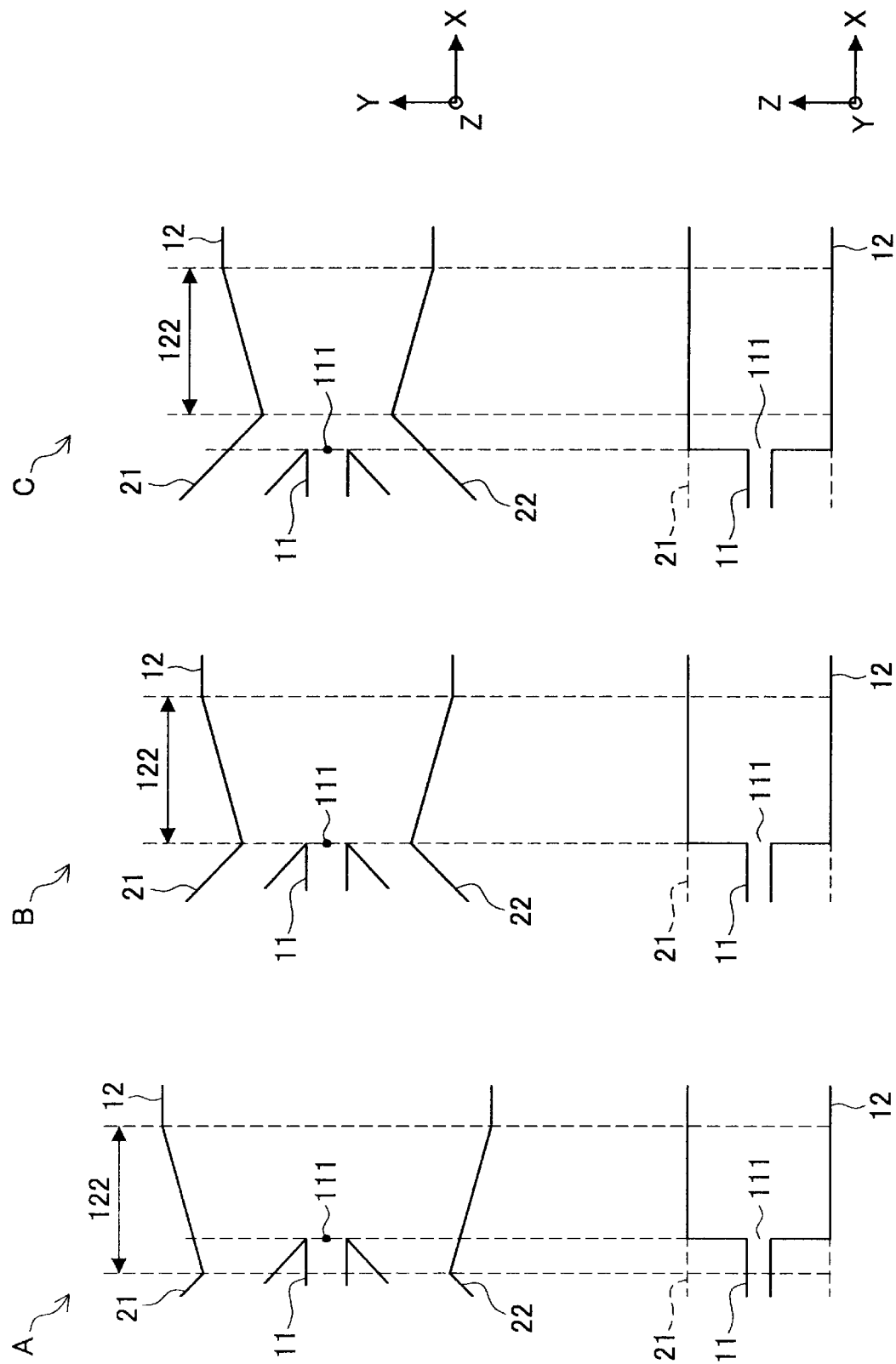
[FIG. 5]

FIGS. 5A, 5B and 5C show alternative examples of the tapered portion 122, in which the upper part shows a top schematic view and the lower part shows a sectional schematic view. As shown in FIG. 5A, for example, the tapered portion 122 may be placed so that the point at which the channel width in the Y-axis direction begins to increase is located on the upstream side of the communicating port 111. Further, as shown in FIG. 5B, the tapered portion 122 may be placed so that the point at which the channel width in the Y-axis direction begins to increase is located at the position coinciding with the communicating port 111. Note that FIG. 5C shows the case where the point at which the channel width in the Y-axis direction begins to increase is located on the downstream side of the communicating port 111 and the tapered portion 122 is placed on the downstream side of the communicating port 111.

4. Microchip According to Second Embodiment of Invention

Figure 6:
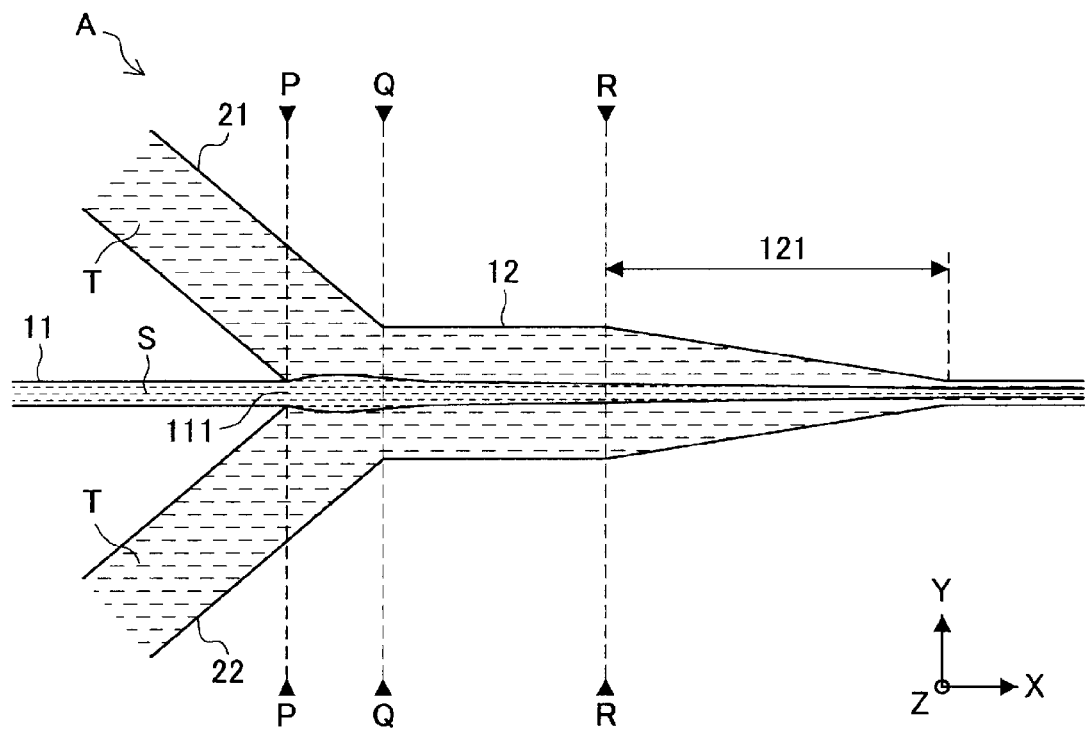
[FIG. 6]
Figure 6:
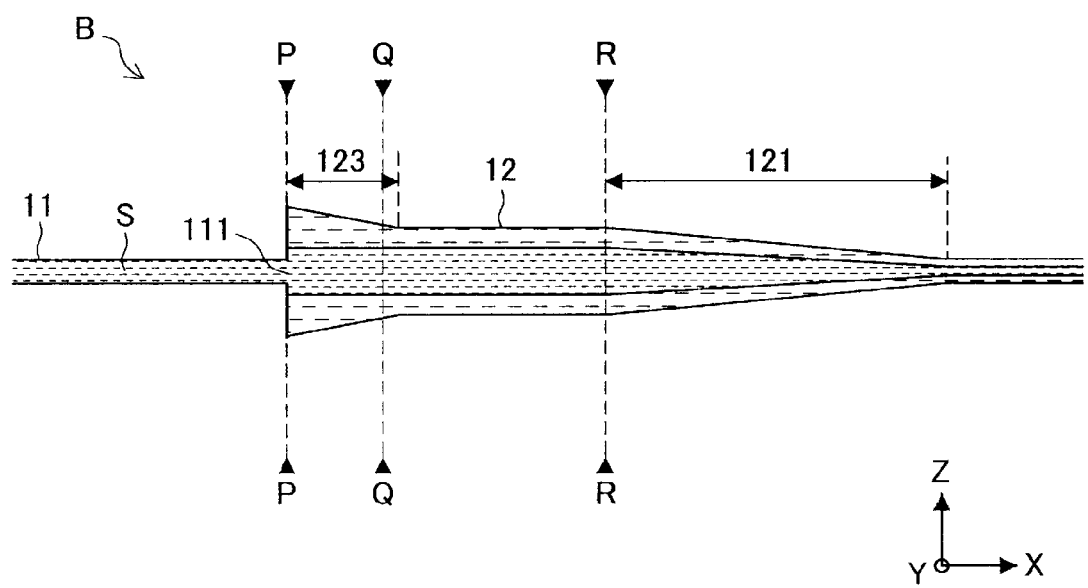

FIGS. 6A and 6B are schematic diagrams illustrating a channel structure on a microchip according to a second embodiment of the present invention, in which FIG. 6A shows a top view and FIG. 6B shows a sectional view.

In the figures, the reference numeral 11 indicates a sample liquid introduction channel through which a sample liquid is introduced. The reference numerals 21 and 22 indicate sheath liquid introduction channels which are arranged to sandwich the sample liquid introduction channel 11 and merged with the sample liquid introduction channel 11 from the both sides thereof, and through a sheath liquid is introduced. Further, the reference numeral 12 indicates a merge channel which is connected to the sample liquid introduction channel 11 and the sheath liquid introduction channels 21 and 22 and through which the sample liquid and the sheath liquids fed from the respective channels are merged and flow.

The sample liquid introduction channel 11 has, at the merging portion with the sheath liquid introduction channels 21 and 22, a communicating port 111 for introducing the sample liquid into the center of the merge channel 12 through which the sheath liquid laminar flow T flows.

The channel depth of the sample liquid introduction channel 11 in the Z-axis direction is designed to be smaller than the channel depth of the sheath liquid introduction channels 21 and 22, and the communicating port 111 is disposed at substantially the center position in the channel depth direction of the sheath liquid introduction channels 21 and 22. Further, the communicating port 111 is also disposed at substantially the center position in the channel width direction (the Y-axis direction) of the merge channel 12.

Figure 7:
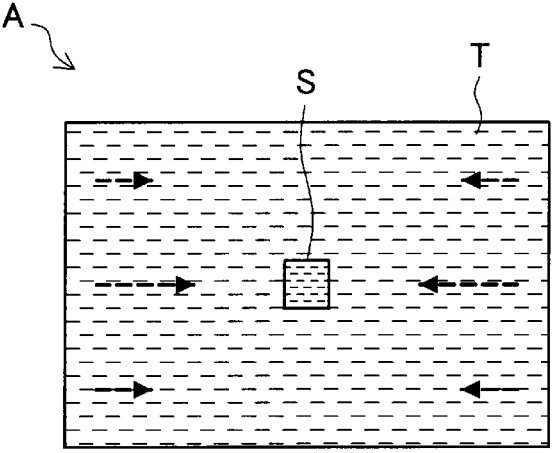
[FIG. 7]
Figure 7:
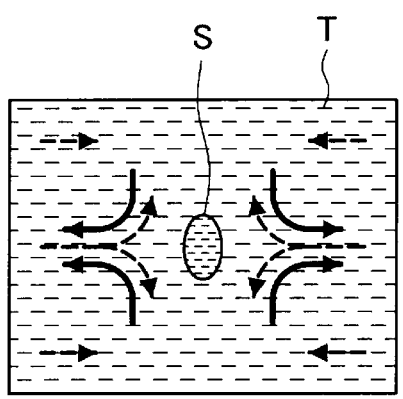
Figure 7:
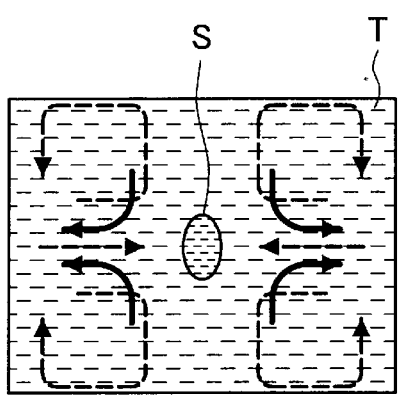

By introducing the sample liquid laminar flow S to the center of the sheath liquid laminar flow T from the communicating port 111, the sample liquid laminar flow S can be fed in the state of being surrounded by the sheath liquid laminar flow T (see also FIG. 7 described next). Note that the position where the communicating port 111 is placed is not limited to the center position of the channel depth direction of the sheath liquid introduction channels 21 and 22 and may be in its vicinity, as long as it allows the sample liquid laminar flow S to be fed into the merge channel 12 in the state of being surrounded by the sheath liquid laminar flow T. Likewise, the position of the communicating port 111 in the channel width direction of the merge channel 12 is not limited to the center position and may be in its vicinity.

In the figures, the reference numeral 123 indicates a tapered portion that functions to suppress the spiral flow field generated after the merging of the sample liquid laminar flow and the sheath liquid laminar flows illustrated in FIG. 20. The tapered portion 123 is disposed in the merge channel 12 in close proximity to the merging portion of the sample liquid introduction channel 11 with the sheath liquid introduction channels 21 and 22. The tapered portion 123 is formed so that the channel depth in the vertical direction (the Z-axis direction) perpendicular to the plane (X-Y plane) containing the sample liquid introduction channel 11 and the sheath liquid introduction channels 21 and 22 is narrowed gradually along the feeding direction.

The fluid velocity vector field in the merge channel 12 and the function of the tapered portion 123 are described with reference to FIGS. 6A and 6B and FIGS. 7A to 7C. FIGS. 7A, 7B and 7C are schematic sectional diagrams of the merge channel 12, in which FIG. 7A shows section P-P, FIG. 7B shows section Q-Q, and FIG. 7C shows section R-R, respectively in FIGS. 6A and 6B.

When the sample liquid laminar flow S is introduced from an opening 111 into the center of the sheath liquid laminar flow T flowing through the merge channel 12, a high velocity vector appears at the center in the depth direction of the channel immediately after the introduction (see the dotted-line arrows in FIG. 7A). The high velocity vector occurs because the merged sample liquid laminar flow S and sheath liquid laminar flows T are concentrated on the center of the depth direction of the channel for flowing faster as described earlier.

At the tapered portion 123, when the laminar flow width of the merged sample liquid laminar flow S and sheath liquid laminar flow T is narrowed in the Z-axis direction, a flow field (see the solid-line arrows in FIG. 7B), which is in reverse direction to the high velocity vector generated at the center in the depth direction of the channel, is generated. By generating the reverse flow field, the tapered portion 123 cancels out the flow field generated at the center in the depth direction of the channel and thereby prevents the flow field from growing into the spiral flow field. As a result, the sample liquid laminar flow S is maintained in the state of being converted to the center of the channel without being stretched out in the Z-axis direction by the spiral flow field (see FIGS. 7B and 7C).

In the figures, the reference numeral 121 indicates a contracted portion that functions to narrow down the laminar flow width of the merged sample liquid laminar flow S and sheath liquid laminar flow T in the Y-axis direction and the Z-axis direction. The structure and the action of the contracted portion 121 are the same as those in the microchip according to the first embodiment and not redundantly described. Further, the structure and the action of the communicating port 111 are also the same as those in the microchip according to the first embodiment.

5. Alternative Example of Channel Structure of Microchip According to Second Embodiment FIG. 6B illustrates the case where the tapered portion 123 is disposed so that the point at which the channel depth in the Z-axis direction begins to decrease coincides with the position of the communicating port 111. However, the position where the tapered portion 123 is disposed is not limited to the position shown in FIG. 6B, as long as it is in close proximity to the merging portion of the sample liquid introduction channel 11 with the sheath liquid introduction channels 21 and 22.

Figure 8:
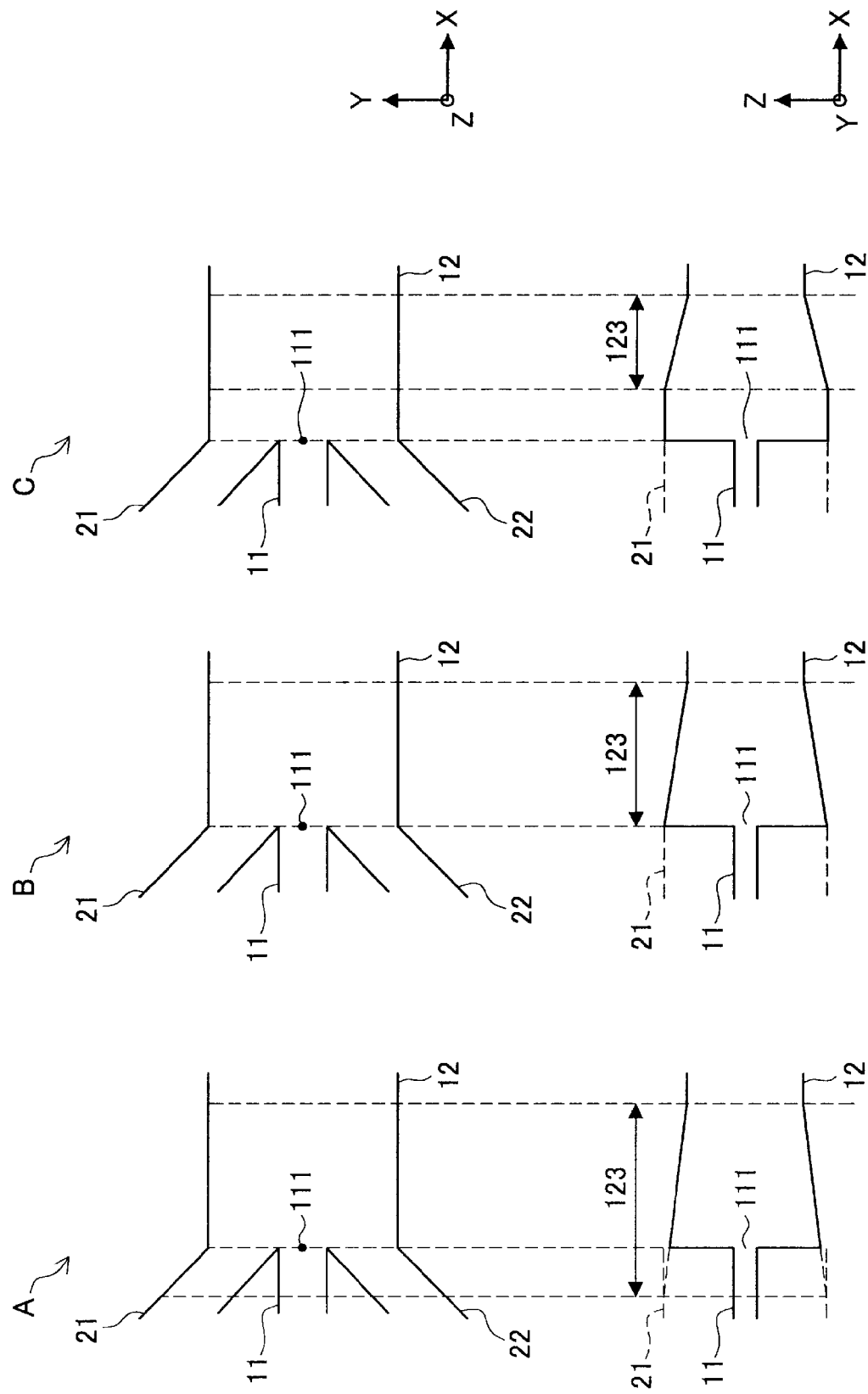
[FIG. 8]

FIGS. 8A, 8B and 8C show alternative examples of the tapered portion 123, in which the upper part shows a top schematic view and the lower part shows a sectional schematic view, of the tapered portion 123. As shown in FIG. 8A, for example, the tapered portion 123 may be placed so that the point at which the channel depth in the Z-axis direction begins to decrease is located on the upstream side of the communicating port 111. Further, as shown in FIG. 8C, the tapered portion 123 may be placed so that the point at which the channel depth in the Z-axis direction begins to decrease is located on the downstream side of the communicating port 111. Note that FIG. 8B shows the case where the point at which the channel depth in the Z-axis direction begins to decrease is located at the position coinciding with the communicating port 111 as in the case of FIGS. 6A and 6B.

Figure 9:
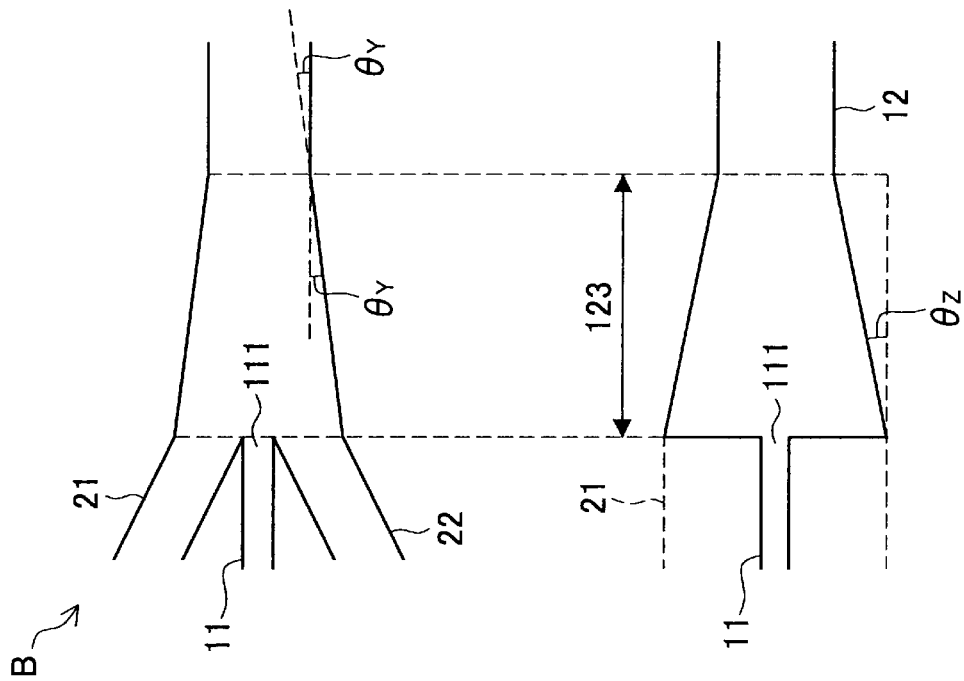
[FIG. 9]
Figure 9:
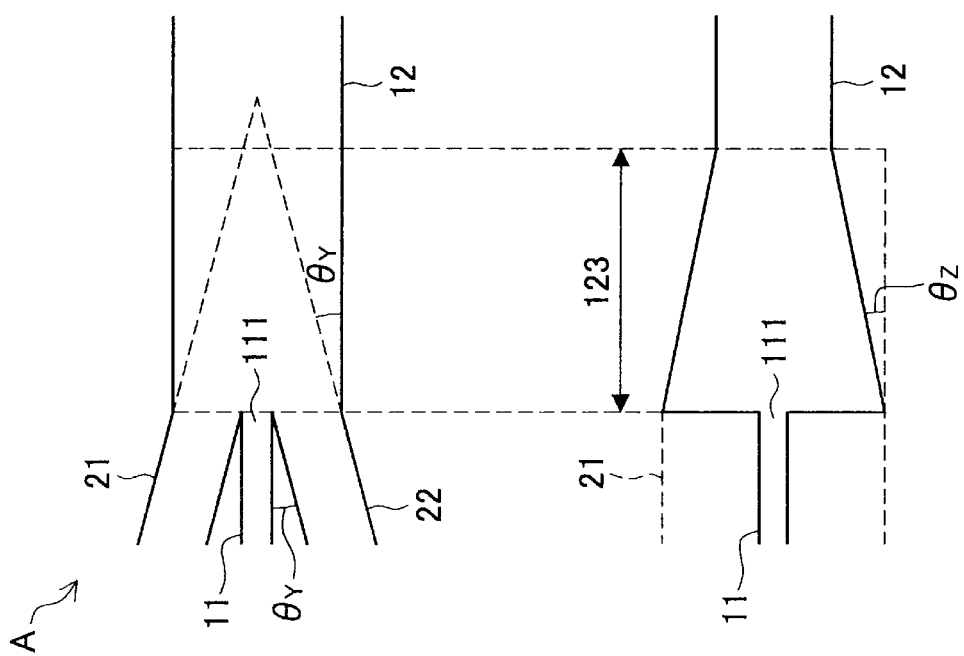

A taper angle (see the symbol $(\theta)z$ in FIGS. 9A and 9B) in the channel depth direction of the tapered portion 123 may be set to any value as long as the function of the tapered portion 123 can be exerted. By setting the taper angle $(\theta)z$ to be larger than the merging angle (see the symbol (theta)y in FIG. 9A) of the sheath liquid introduction channels 21 and 22 with the sample liquid introduction channel 11, the effect of suppressing the generation of the spiral flow field can be enhanced. Further, in the case where the channel width of the merge channel 12 is designed to be reduced gradually along the feeding direction, by setting the taper angle (theta)z to be larger than the draw angle (see the symbol (theta)y in FIG. 9B) of the merge channel 12, the sufficient effect of suppressing the spiral flow field can be obtained.

Figure 10:
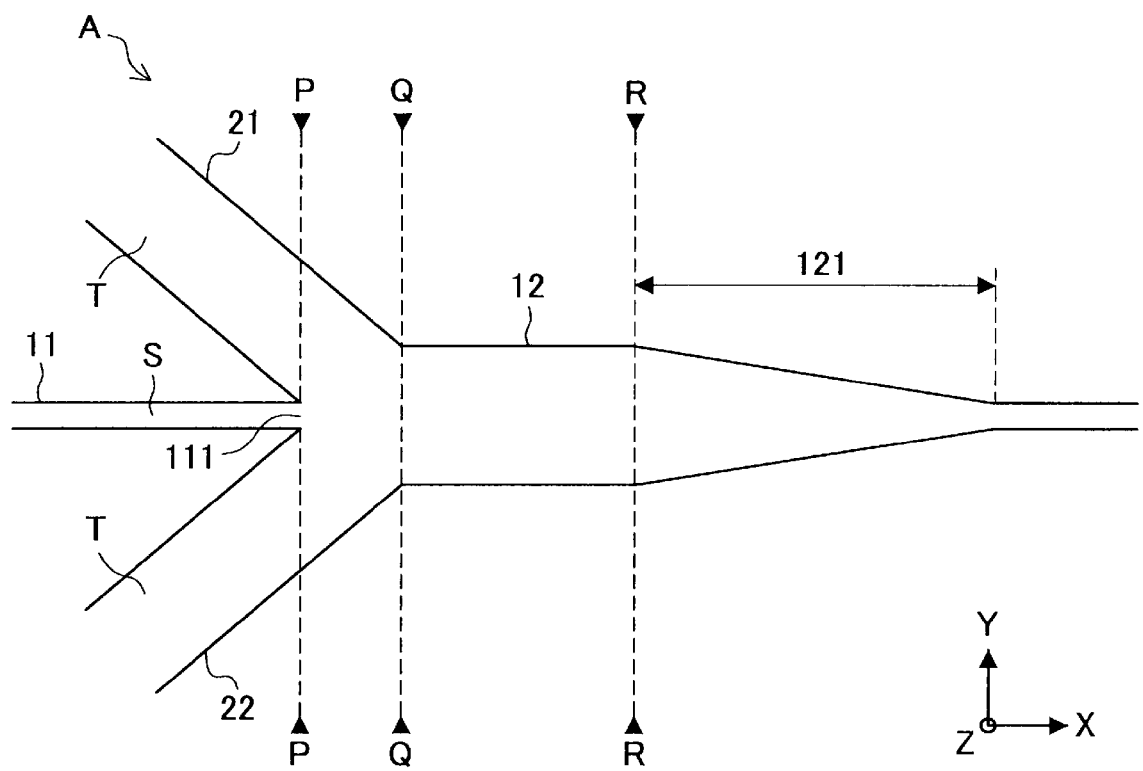
[FIG. 10]
Figure 10:
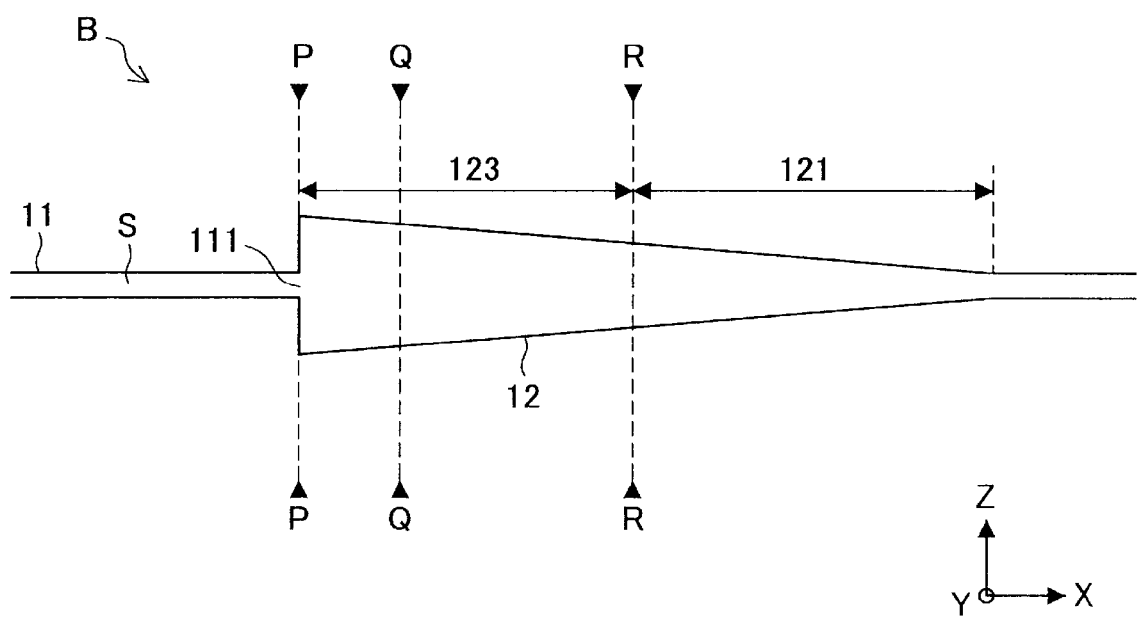

Although the case where the tapered portion 123 and the contracted portion 121 are formed discontinuously is illustrated in FIGS. 6A and 6B, the tapered portion 123 and the contracted portion 121 may be formed continuously as illustrated in FIGS. 10A and 10B.

6. Microchip According to Third Embodiment of Invention

Figure 11:
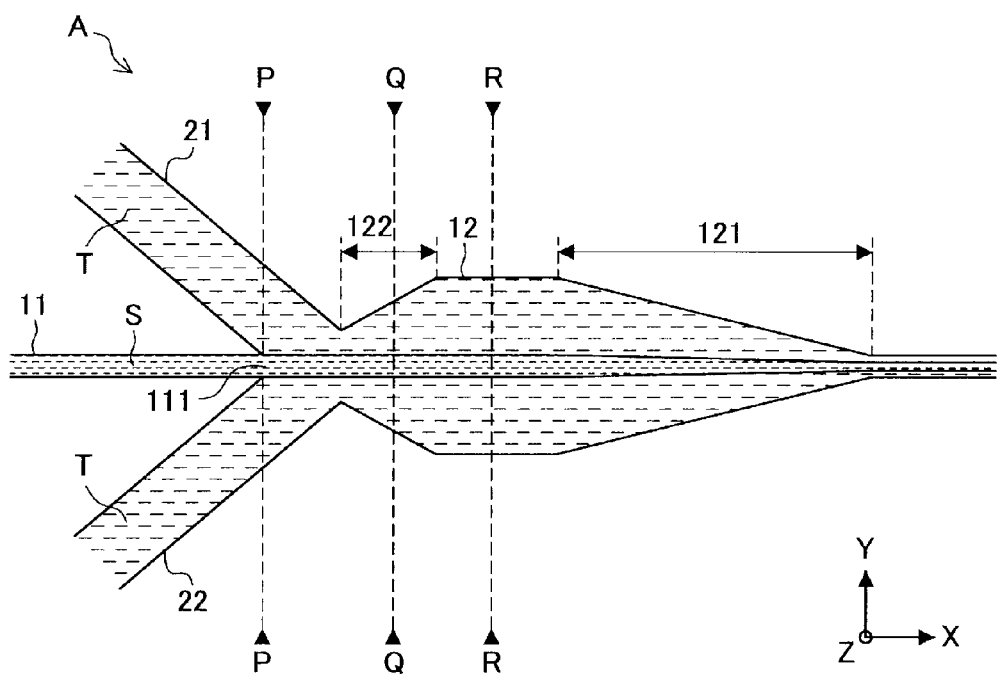
[FIG. 11]
Figure 11:
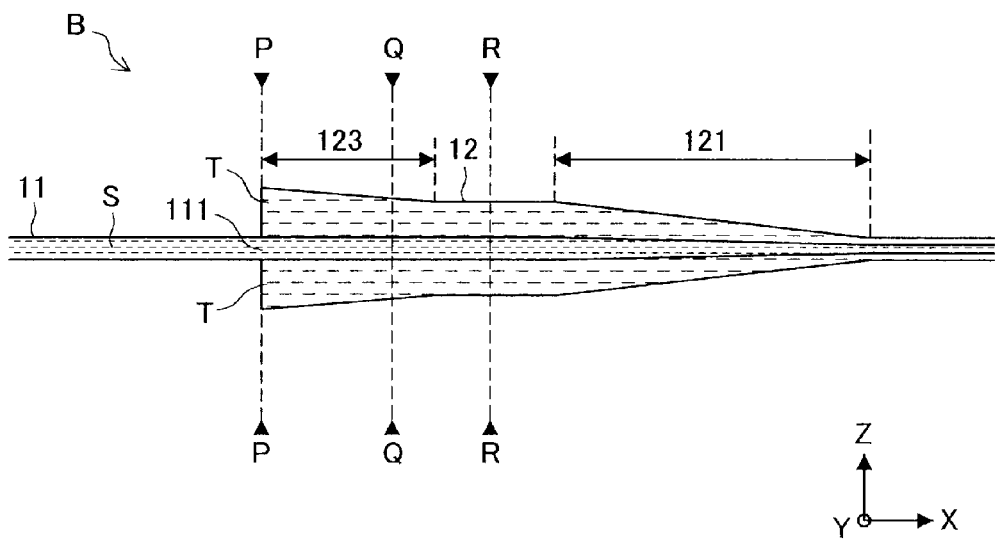

FIGS. 11A and 11B are schematic diagrams illustrating a channel structure on a microchip according to a third embodiment of the present invention, in which FIG. 11A shows a top view and FIG. 11B shows a sectional view, respectively of the microchip.

In the figures, the reference numeral 11 indicates a sample liquid introduction channel through which a sample liquid is introduced. The reference numerals 21 and 22 indicate sheath liquid introduction channels which are arranged to sandwich the sample liquid introduction channel 11 and merged with the sample liquid introduction channel 11 from the both sides thereof, and through a sheath liquid is introduced. Further, the reference numeral 12 indicates a merge channel which is connected to the sample liquid introduction channel 11 and the sheath liquid introduction channels 21 and 22 and through which the sample liquid and the sheath liquids fed from the respective channels are merged and flow.

The sample liquid introduction channel 11 has, at the merging portion with the sheath liquid introduction channels 21 and 22, a communicating port 111 for introducing the sample liquid into the center of the merge channel 12 through which the sheath liquid laminar flow T flows.

The channel depth of the sample liquid introduction channel 11 in the Z-axis direction is designed to be smaller than the channel depth of the sheath liquid introduction channels 21 and 22, and the communicating port 111 is disposed at substantially the center position in the channel depth direction of the sheath liquid introduction channels 21 and 22. Further, the communicating port 111 is also disposed at substantially the center position in the channel width direction (the Y-axis direction) of the merge channel 12.

Figure 12:
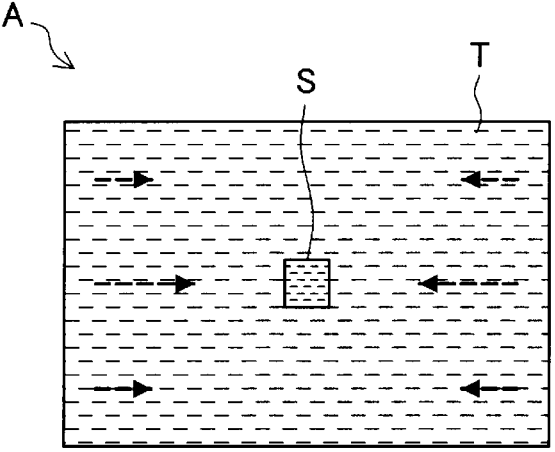
[FIG. 12]
Figure 12:
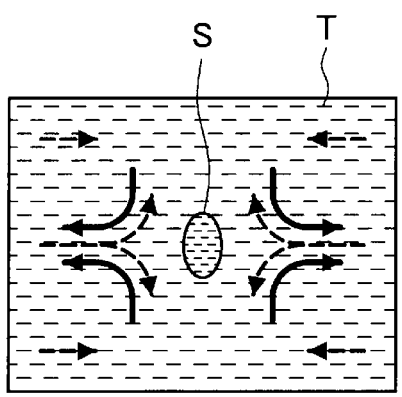
Figure 12:
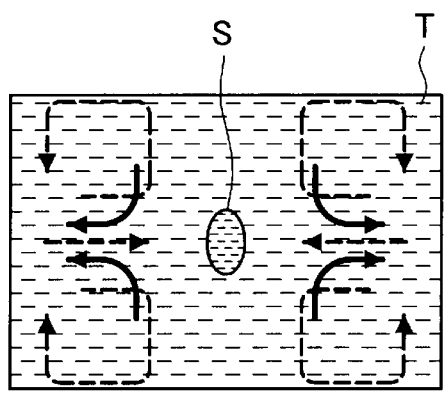

By introducing the sample liquid laminar flow S to the center of the sheath liquid laminar flow T from the communicating port 111, the sample liquid laminar flow S can be fed in the state of being surrounded by the sheath liquid laminar flow T (see also FIG. 12 described next). Note that the position where the communicating port 111 is placed is not limited to the center position of the channel depth direction of the sheath liquid introduction channels 21 and 22 and may be in its vicinity, as long as it allows the sample liquid laminar flow S to be fed into the merge channel 12 in the state of being surrounded by the sheath liquid laminar flow T. Likewise, the position of the communicating port 111 in the channel width direction of the merge channel 12 is not limited to the center position and may be in its vicinity.

In the figures, the reference numerals 122 and 123 indicate tapered portions that function to suppress the spiral flow field generated after the merging of the sample liquid laminar flow and the sheath liquid laminar flows illustrated in FIG. 20. The tapered portions 122 and 123 are disposed in the merge channel 12 in close proximity to the merging portion of the sample liquid introduction channel 11 with the sheath liquid introduction channels 21 and 22. The tapered portion 122 is formed so that the channel width in the sandwiching direction (the Y-axis direction) along which the sample liquid introduction channel 11 is sandwiched by sheath liquid introduction channels 21 and 22 is enlarged gradually along the feeding direction. Further, the tapered portion 123 is formed so that the channel depth in the vertical direction (the Z-axis direction) perpendicular to the plane (X-Y plane) containing the sample liquid introduction channel 11 and the sheath liquid introduction channels 21 and 22 is narrowed gradually along the feeding direction. In the microchip according to the embodiment, the tapered portions 122 and 123 are formed in a partially overlap area of the merge channel 12.

The fluid velocity vector field in the merge channel 12 and the function of the tapered portions 122 and 123 are described with reference to FIGS. 11A and 11B and FIGS. 12A to 12C. FIGS. 12A, 12B and 12C are schematic sectional diagrams of the merge channel 12, in which FIG. 12A shows section P-P, FIG. 12B shows section Q-Q, and FIG. 12C shows section R-R, respectively in FIGS. 11A and 11B.

When the sample liquid laminar flow S is introduced from an opening 111 into the center of the sheath liquid laminar flow T flowing through the merge channel 12, a high velocity vector appears at the center in the depth direction of the channel immediately after the introduction (see the dotted-line arrows in FIG. 12A). The high velocity vector occurs because the merged sample liquid laminar flow S and sheath liquid laminar flows T are concentrated on the center of the depth direction of the channel for flowing faster as described earlier.

At the tapered portion 122, when the laminar flow width of the merged sample liquid laminar flow S and sheath liquid laminar flow T is enlarged in the Y-axis direction, and at the tapered portion 123, when the laminar flow width of the merged sample liquid laminar flow S and sheath liquid laminar flow T is narrowed in the Z-axis direction, a flow field (see the solid-line arrows in FIG. 12B), which is in reverse direction to the high velocity vector generated at the center in the depth direction of the channel, is generated. By generating the reverse flow field, the tapered portions 122 and 123 cancel out the flow field generated at the center in the depth direction of the channel and thereby prevent the flow field from growing into the spiral flow field. As a result, the sample liquid laminar flow S is maintained in the state of being converted to the center of the channel without being stretched out in the Z-axis direction by the spiral flow field (see FIGS. 12B and 12C).

In the figures, the reference numeral 121 indicates a contracted portion that functions to narrow down the laminar flow width of the merged sample liquid laminar flow S and sheath liquid laminar flow T in the Y-axis direction and the Z-axis direction. The structure and the action of the contracted portion 121 are the same as those in the microchip according to the first embodiment and not redundantly described. Further, the structure and the action of the communicating port 111 are also the same as those in the microchip according to the first embodiment.

7. Alternative Example of Channel Structure of Microchip According to Third Embodiment FIG. 11A illustrates the case where the tapered portion 122 is disposed in the merge channel 12 on the downstream side of the communicating port 111, which is the merging portion of the sample liquid introduction channel 11 with the sheath liquid introduction channels 21 and 22. However, the position where the tapered portion 122 is disposed is not limited to the position shown in FIG. 11A, as long as it is in close proximity to the merging portion of the sample liquid introduction channel 11 with the sheath liquid introduction channels 21 and 22.

Further, FIG. 11B illustrates the case where the tapered portion 123 is disposed so that the point at which the channel depth in the Z-axis direction begins to decrease coincides with the position of the communicating port 111. However, the position where the tapered portion 123 is disposed is not limited to the position shown in FIG. 11B, as long as it is in close proximity to the merging portion of the sample liquid introduction channel 11 with the sheath liquid introduction channels 21 and 22.

Furthermore, FIGS. 11A and 11B illustrate the case where the point of the tapered portion 123 at which the channel depth in the Z-axis direction begins to decrease is disposed on the upstream side of the point of the tapered portion 122 at which the channel width in the Y-axis direction begins to increase. However, the point at which the tapered portion 122 begins and the point at which the tapered portion 123 begins may be different or the same. Likewise, although FIGS. 11A and 11B illustrate the case where the point of the tapered portion 122 at which the channel width in the Y-axis direction ends to increase and the point of the tapered portion 123 at which the channel depth in the Z-axis direction ends to decrease are disposed on the same position, the point at which the tapered portion 122 ends and the point at which the tapered portion 123 ends may be different or the same.

Figure 13:
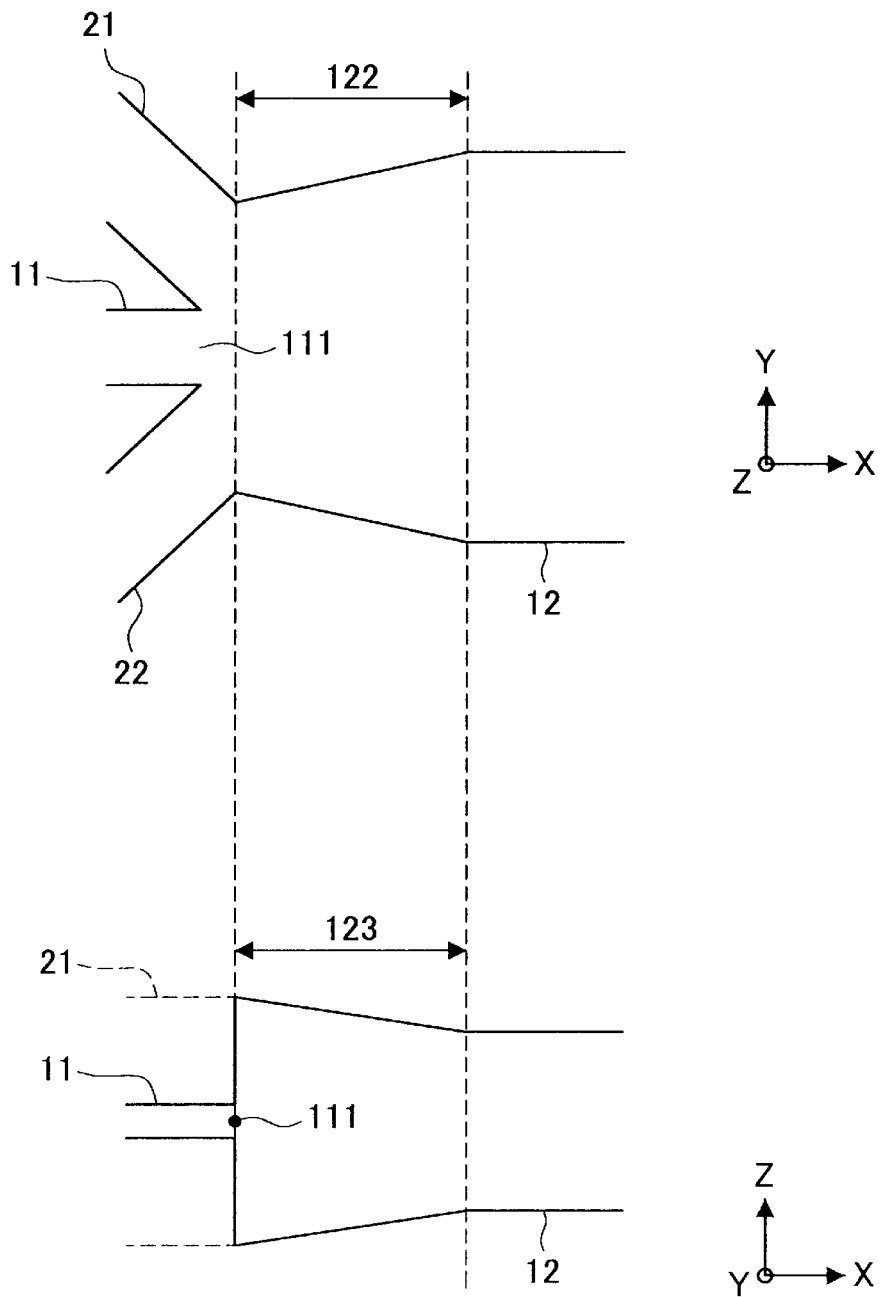
[FIG. 13]

FIG. 13 shows an alternative example of the tapered portions 122 and 123. In this alternative example, the positions of the point of the tapered portion 122 at which the channel width in the Y-axis direction begins to increase and the point of the tapered portion 123 at which the channel depth in the Z-axis direction begins to decrease both coincide with the communicating port 111. Further, the positions of the point at which the tapered portion 122 ends and the point at which the tapered portion 123 ends also coincide with each other.

Figure 14:
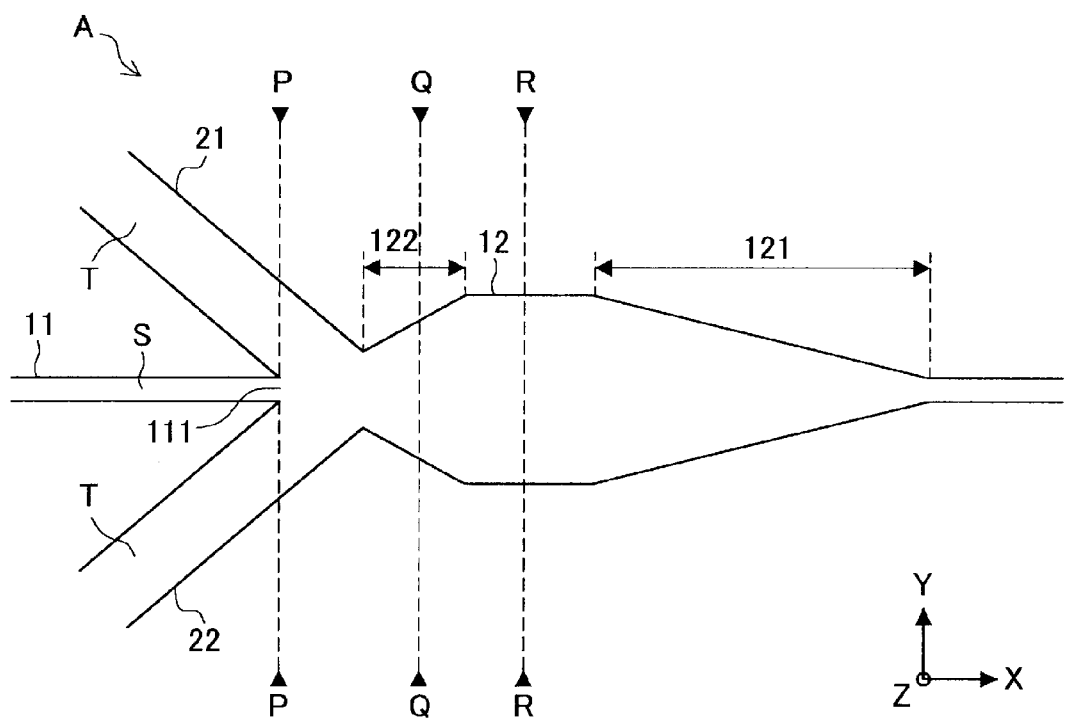
[FIG. 14]
Figure 14:
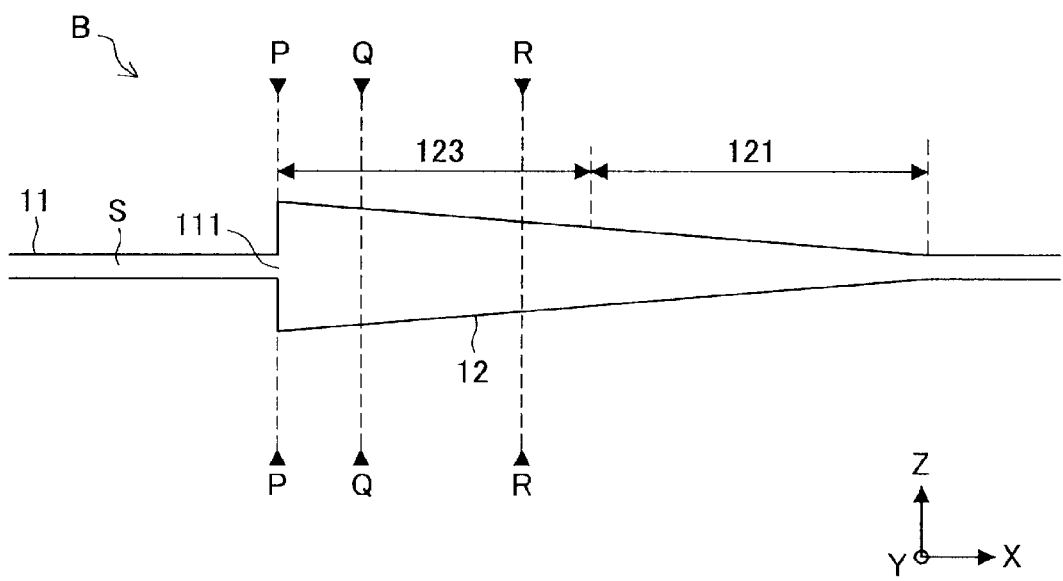

Further, although the case where the tapered portion 123 and the contracted portion 121 are formed discontinuously is illustrated in FIGS. 11A and 11B, the tapered portion 123 and the contracted portion 121 may be formed continuously as illustrated in FIGS. 14A and 14B.

8. Manufacturing of Microchip According to Invention

The material of the microchip according to the embodiment of the present invention may be glass or various kinds of plastic (PP, PC, COP, PDMS). In the case where the analysis using the microchip is carried out optically, it is preferred to select a material having light transmittance, with low autofluorescence, and with small optical errors because of small wavelength dispersion.

In order to maintain the light transmittance of the microchip, its surface is preferably coated with a so-called hard coat layer which is used for an optical disc. If a stain such as fingerprints is attached to the surface of the microchip, particularly, the surface of an optical detector, the amount of light transmission decreases to cause the degradation of accuracy of optical analyses. By depositing the hard coat layer with high transparency and stain resistance on the surface of the microchip, the degradation of accuracy of analysis can be prevented.

The hard coat layer can be formed by use of one of the hard coating agents which are used ordinarily, for example, a UV-curing type hard coating agent admixed with a fingerprint stain-proofing agent such as a fluoro or silicone stain-proofing agent. Japanese Patent Laid-open No. 2003-157579 discloses an active energy ray curable composition (P) as a hard-code agent which contains a multifunctional compound (A) having at least two polymerizable functional groups capable of being polymerized under active energy rays, modified colloidal silica (B) whose average particle diameter is 1 to 200 nm, and whose surface has been modified by a mercaptosilane compound in which an organic group having a mercapto group and a hydrolysable group or hydroxyl group are bonded to silicon atom, and a photopolymerization initiator (C).

Forming of the sample liquid introduction channel 11, the sheath liquid introduction channels 21 and 22, the merge channel 12 having the tapered portions 122 and 123 and the contracted portion 121 and the like arranged in the microchip can be carried out by wet etching or dry etching of a glass-made substrate layer, or by nanoimprint technique or injection molding or cutting of a plastic-made substrate layer. Then, the two substrates on which the sample liquid introduction channel 11 and the like is formed are laminated onto each other, whereby the microchip can be fabricated. The lamination of the substrates onto each other can be carried out by appropriately using a known method, such as heat fusing, adhesion with an adhesive, anodic bonding, bonding by use of a pressure sensitive adhesive-coated sheet, plasma-activated bonding, ultrasonic bonding, etc.

Figure 15:
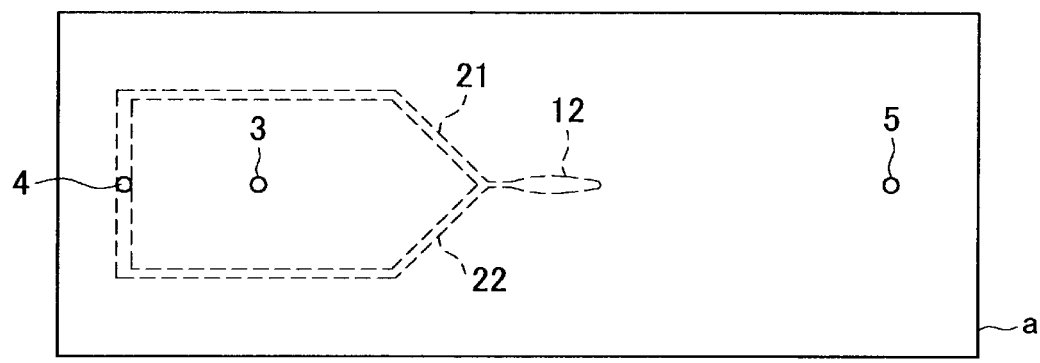
[FIG. 15]
Figure 15:
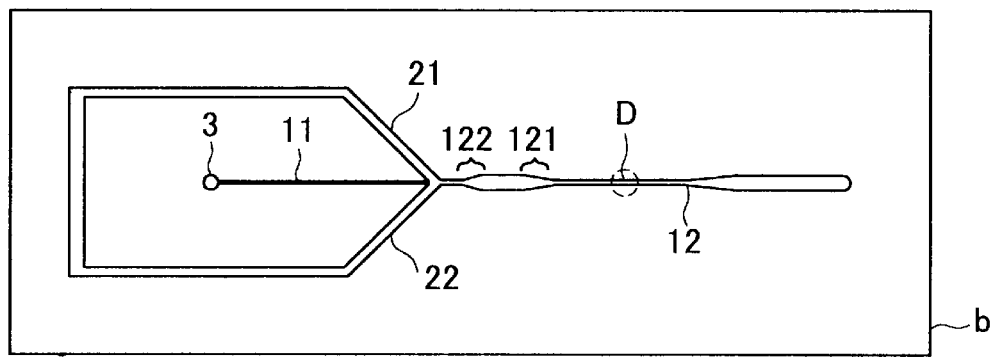
Figure 16:
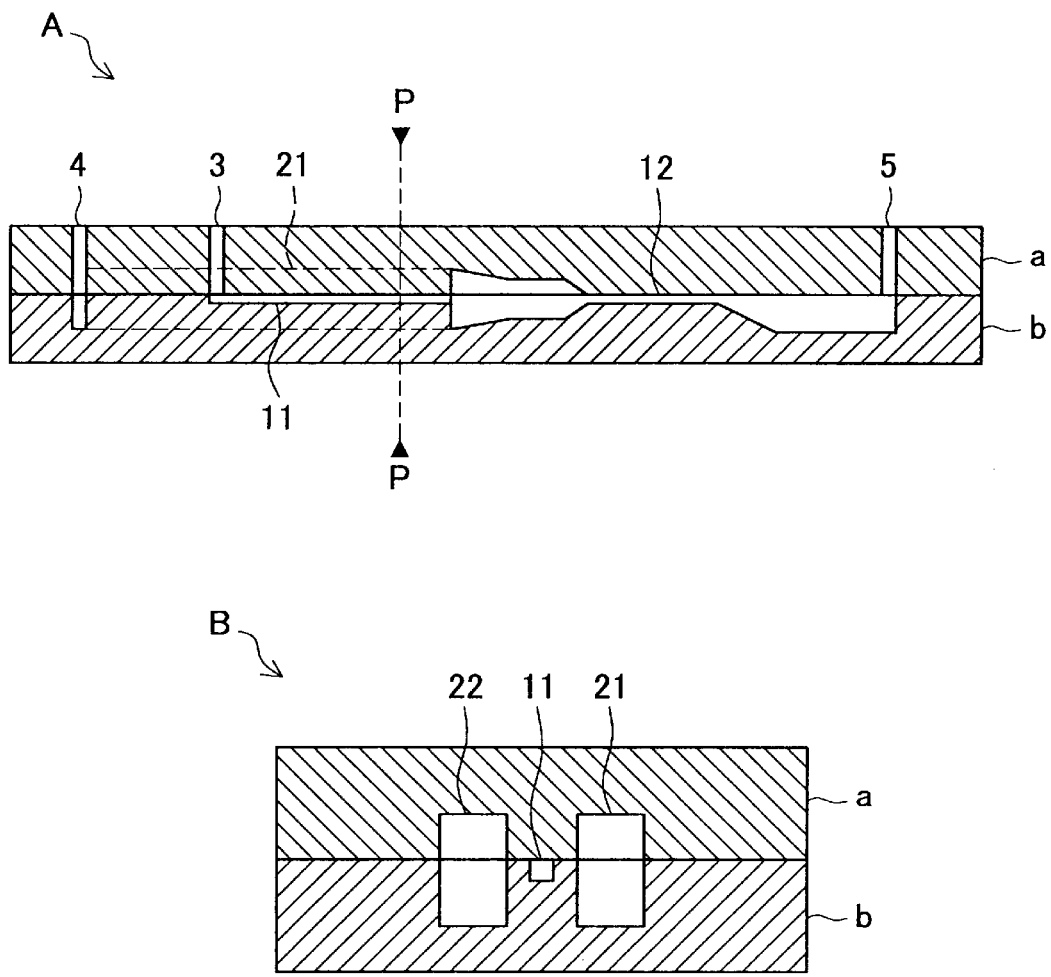
[FIG. 16]
Figure 17:
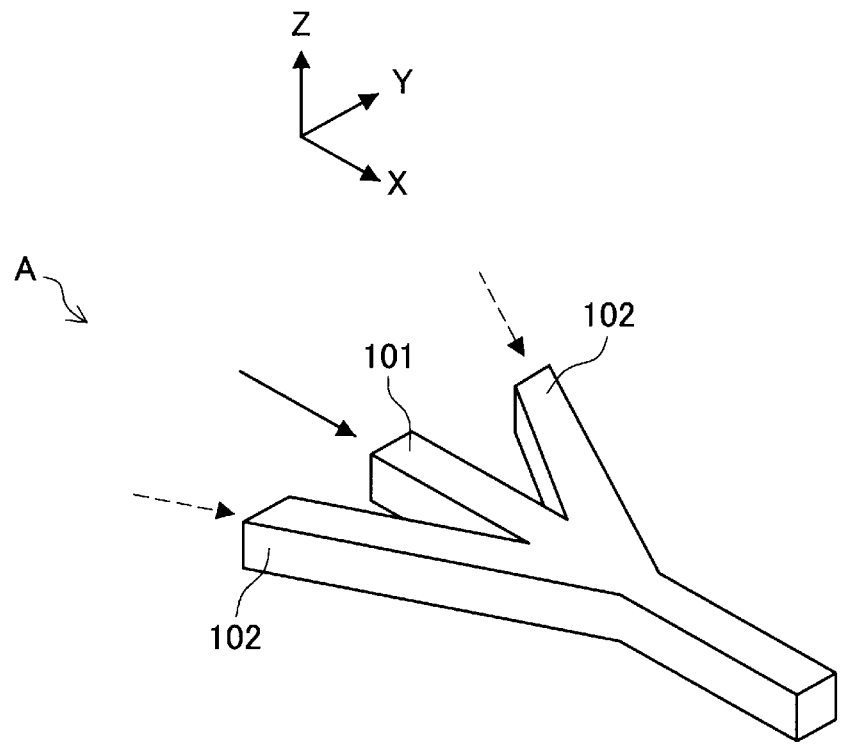
[FIG. 17]
Figure 17:
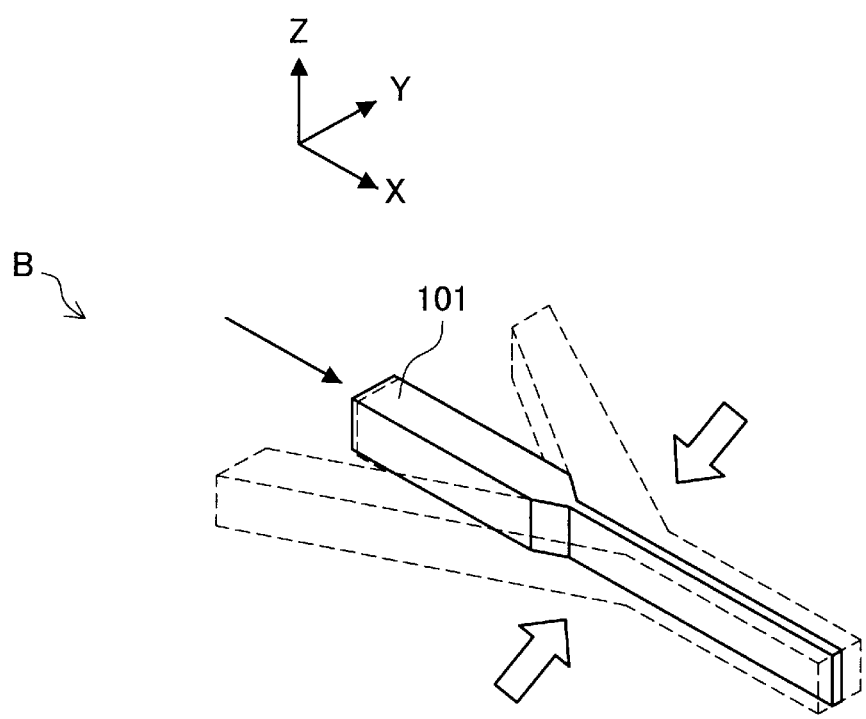

A manufacturing method of the microchip according to the embodiment of the present invention is described hereinafter with reference to FIGS. 15A and 15B and FIGS. 16A and 16B. FIGS. 15A and 15B show top schematic diagrams of substrates constituting the microchip according to the embodiment of the present invention. FIGS. 16A and 16B show sectional diagrams of the microchip according to the embodiment of the present invention. FIG. 16B shows section P-P in FIG. 16A.

First, part of the sheath liquid introduction channels 21 and 22 and part of the merge channel 12 are made on a substrate a (see FIG. 15A). On the substrate a, a sample liquid supply port 3 for supplying a sample liquid to the sample liquid introduction channel 11, a sheath liquid supply port 4 for supplying a sheath liquid to the sheath liquid introduction channels 21 and 22, and an discharge port for discharging the sample liquid and the sheath liquid from the merge channel 12 are also made. Next, the sample liquid introduction channel 11, part of the sheath liquid introduction channels 21 and 22 and part of the merge channel 12 are made on a substrate b (see FIG. 15B).

Next, the substrate a and the substrate b are laminated onto each other by thermocompression bonding or the like as shown in FIGS. 16A and 16B, whereby the microchip can be fabricated. In this step, the sheath liquid introduction channels 21 and 22 are created at different depths on the substrates a and b so that the sample liquid introduction channel 11 is located at substantially the center in the channel depth direction of the sheath liquid introduction channels 21 and 22.

As described above, the microchip according to the embodiment of the present invention may be manufactured by laminating the substrates a and b on which the sample liquid introduction channel 11 and the like is made. Therefore, differently from the microchip disclosed in the above-described Patent Literature 2 in which the guide structure is provided at the opening of the channel for introducing the sample liquid laminar flow, the microchip according to the embodiment of the present invention can be manufactured by the lamination of two substrates only. The formation of the channel structure onto each substrate and the lamination of the substrates are thus easy, thereby suppressing the manufacturing cost of the microchip.

9. Particulate Analyzing Device According to Invention

The above-described microchip can be incorporated into a particulate analyzing device according to an embodiment of the present invention. The particulate analyzing device is applicable as a particulate fractionating device that analyzes the characteristics of particulates and performs fractionation of particulates on the basis of the analytical results.

In the particulate analyzing device, a detector (see the symbol D in FIG. 15B) for detecting particulates contained in the sample liquid fed from the sample liquid introduction channel 11 is placed on the downstream side of the tapered portion 122 or 123 and the contracted portion 121 in the merge channel 12 of the microchip.

Figure 2:
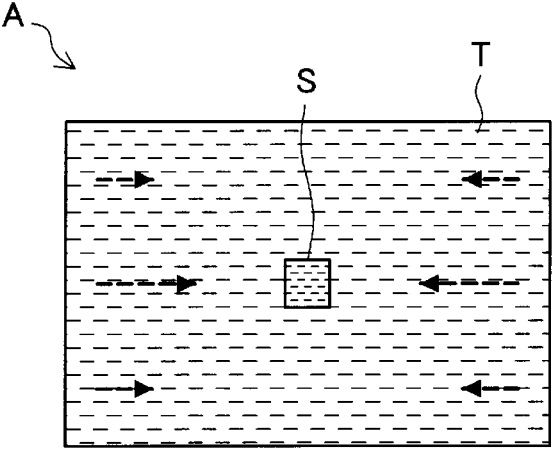
[FIG. 2]
Figure 2:
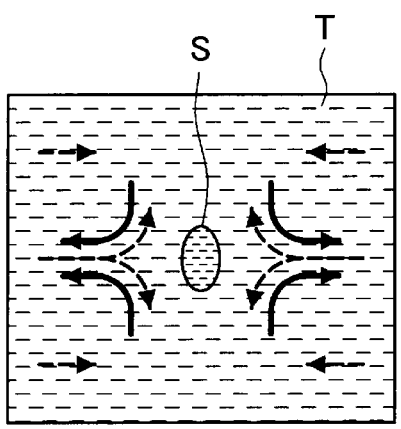
Figure 2:
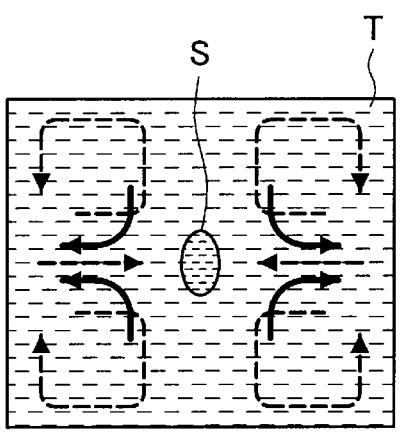
Figure 2:
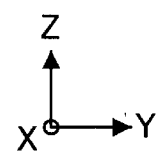

The microchip according to the embodiment of the present invention makes it possible, with the tapered portion 122, 123, to feed the sample liquid laminar flow S in the state of being converted to the center of the merge channel 12 and thereby eliminate the dispersion of the feeding position of the particulates in the depth direction of the channel and the difference in the flowing speed of the particulates caused by the dispersion (see FIG. 2 etc.). Thus, by placing the detecting portion D on the downstream side of the tapered portion 122, 123 and detecting particulates, it is possible to eliminate the variation of detection signals caused by the difference in the flowing speed of the particulates and thereby achieve the detection of particulates with high accuracy.

Further, the microchip according to the embodiment of the present invention makes it possible, with the contracted portion 121, to feed the liquids by narrowing down the laminar flow width of the sample liquid laminar flow S and the sheath liquid laminar flow T in the channel width direction and depth direction. By narrowing down the laminar flow width of the sample liquid laminar flow S and the sheath liquid laminar flow T, the particulates can be made to be arranged in a row in the sample liquid laminar flow S, and the dispersion of the feeding position of the particulates in the depth direction of the channel and the difference in the flowing speed of the particulates caused by the dispersion can be further reduced. Thus, by placing the detecting portion D on the downstream side of the contracted portion 121 and detecting particulates, it is possible to detect the particulates one by one and also make detection by eliminating the variation of detection signals caused by the difference in the flowing speed of the particulates as much as possible.

The detecting portion D may be configured as an optical detection system, an electrical detection system, or a magnetic detection system. Those detection systems may be configured in the same manner as those in particulate analyzing systems using microchips according to related art.

Specifically, the optical detection system includes a laser beam source, an irradiation section composed of a condenser lens and the like for condensing the laser beam and irradiating each of the particulates with the laser beam, and a detection system for detecting the light generated from the particulate upon irradiation with the laser beam by use of a dichroic minor, a bandpass filter and the like. The detection of the light generated from particulates may be made by an area image pick-up element such as a PMT (photo multiplier tube), a CCD or a CMOS device, for example.

Further, the electrical detection system or the magnetic detection system places micro-electrodes on the channel of the detecting portion D and thereby measure, for example, resistance, capacitance, inductance, impedance, variation in electric field between the electrodes or the like, or, alternatively, magnetization, variation in magnetic field or the like.

The light, resistance, magnetization or the like generated from the particulates detected in the detecting portion D is converted into an electrical signal and output to a total control unit. Note that the light to be detected may be forward scattered light or side-way scattered light from the particulate, or scattered light, fluorescent light or the like arising from Reyleigh scattering, Mie scattering or the like.

Based on the electrical signal inputted, the total control unit measures the optical characteristics of the particulates. A parameter for the measurement of the optical characteristics is selected according to the particulates under consideration and the purpose of fractional collection. Specifically, forward scattered light is adopted in the case of determining the size of the particulates, side-way scattered light is adopted in the case of determination of structure, and fluorescent light is adopted in the case of determining whether a fluorescent material labeling the particulate is present or absent.

Further, the particulate analyzing device according to the embodiment of the present invention may be provided with the particulate fractionating channel as disclosed in the above Patent Literature 1 and an electrode for controlling the moving direction of particulates disposed near a channel port to the particulate fractionating channel, so as to analyze the characteristics of the particulates by the total control unit and perform fractionation of the particulates based on the analytical results.

Industrial Applicability

The microchip according to the embodiment of the present invention is easily manufacturable and capable of feeding the sample liquid laminar flow being converged to the center of the channel. Therefore, when analyzing the characteristics of particulates by feeding a solution containing the particulates as a sample liquid through the channel, high analysis accuracy can be obtained by eliminating the dispersion of the feeding position of the particulates in the depth direction of the channel. Therefore, the microchip according to the embodiment of the present invention is suitably applicable to the particulate analyzing technology which analyzes the characteristics of particulates such as cells and microbeads optically, electrically or magnetically.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST

11 First introduction channel (Sample liquid introduction channel)
111 Communication port
12 Merge channel
121 Contracted portion
122, 123 Tapered portion
21, 22 Second introduction channel (Sheath liquid introduction channel)
3 Sample liquid supply port
4 Sheath liquid supply port
5 Discharge port
a, b Substrate
D Detecting portion
S Sample liquid laminar flow
T Sheath liquid laminar flow

The invention claimed is:

1. A microchip comprising:
   a substrate including a fluid channel structure, the fluid channel structure including a first fluid introduction channel and a second fluid introduction channel configured to meet so as to allow merging of a first fluid introduced from the first fluid channel and a second fluid introduced from the second fluid introduction channel, a tapered portion configured to be positioned after merging the first fluid and the second fluid from the first and second fluid introduction channels, and a contracted portion positioned downstream of the tapered portion, wherein the tapered portion and the contracted portion are spaced apart.

2. The microchip according to claim 1, wherein the tapered portion is configured to linearly increase in a first direction.

3. The microchip according to claim 2, wherein the first direction is a Y-axis direction.

4. The microchip according to claim 1, wherein the tapered portion is configured to linearly decrease in a second direction.

5. The microchip according to claim 4, wherein the second direction is a Z-axis direction.

6. The microchip according to claim 1, wherein the tapered portion is configured to linearly increase in a first direction and linearly decrease in a second direction.

7. The microchip according to claim 6, wherein the first direction is a Y-axis direction and the second direction is a Z-axis direction.

8. The microchip according to claim 1, wherein the first fluid introduction channel includes a communication port positioned at substantially a center position of a channel depth direction of the second fluid introduction channel.

9. The microchip according to claim 1, wherein the first fluid introduction channel includes a communication port configured to open in an area that includes the second fluid introduction channel.

10. The microchip according to claim 1, wherein a first channel depth of the first fluid introduction channel in a depth direction is smaller than a second channel depth of the second fluid introduction channel in the depth direction.

11. The microchip according to claim 1, wherein the fluid channel structure further includes a constant portion positioned between the first tapered portion and the contracted portion, and having a fixed depth and width.

12. A particulate analyzing device comprising:
a microchip, the microchip including a substrate including a fluid channel structure including a first fluid introduction channel and a second fluid introduction channel configured to meet so as to allow merging of a first fluid introduced from the first fluid channel and a second fluid introduced from the second fluid introduction channel, a tapered portion configured to be positioned after merging the first fluid and the second fluid from the first and second fluid introduction channels, and a contracted portion positioned downstream of the tapered portion, wherein the tapered portion and the contracted portion are spaced apart.

13. The particulate analyzing device according to claim 12, wherein the tapered portion is configured to linearly increase in a first direction.

14. The particulate analyzing device according to claim 13, wherein the first direction is a Y-axis direction.

15. The particulate analyzing device according to claim 12, wherein the tapered portion is configured to linearly decrease in a second direction.

16. The particulate analyzing device according to claim 15, wherein the second direction is a Z-axis direction.

17. The particulate analyzing device according to claim 12, wherein the tapered portion is configured to linearly increase in a first direction and linearly decrease in a second direction.

18. The particulate analyzing device according to claim 17, wherein the first direction is a Y-axis direction and the second direction is a Z-axis direction.

19. The particulate analyzing device according to claim 12, further including a detector configured to detect particulates in fluid and positioned downstream of the contracted portion.

20. The particulate analyzing device according to claim 12, wherein the first fluid introduction channel includes a communication port positioned substantially at a center position of a channel depth direction of the second fluid introduction channel.

21. The particulate analyzing device according to claim 12, wherein the first fluid introduction channel includes a communication port configured to open in an area that includes the second fluid introduction channel.

22. The particulate analyzing device according to claim 12, wherein a first channel depth of the first fluid introduction channel in a depth direction is smaller than a second channel depth of the second fluid introduction channel in the depth direction.

23. A method of manufacturing a microchip comprising:
forming a substrate including a fluid channel structure, the fluid channel structure including a first fluid introduction channel and a second fluid introduction channel configured to meet so as to allow merging of a first fluid introduced from the first fluid channel and a second fluid introduced from the second fluid introduction channel, a tapered portion configured to be positioned after merging the first fluid and the second fluid from the first and second fluid introduction channels, and a contracted portion positioned downstream of the tapered portion, wherein the tapered portion and the contracted portion are spaced apart.

24. The method of claim 23, further comprising producing a particulate analyzing device that includes the microchip.

25. The method of claim 23, wherein the particulate analyzing device further includes a detector configured to detect particulates in fluid and positioned downstream of the contracted portion.

26. A microchip comprising:
a substrate including a fluid channel structure, the fluid channel structure including a first fluid introduction channel and a second fluid introduction channel configured to meet so as to allow merging of a first fluid introduced from the first fluid channel and a second fluid introduced from the second fluid introduction channel, a tapered portion positioned after merging the first fluid and the second fluid from the first and second fluid introduction channels, a contracted portion positioned downstream of the tapered portion, and a constant portion positioned between the tapered portion and the contracted portion, and having a fixed depth and width, wherein the tapered portion is configured to linearly decrease in Z-axis direction.

* * * * *